(12) United States Patent
Kojima et al.

(10) Patent No.: US 7,189,526 B2
(45) Date of Patent: Mar. 13, 2007

(54) APPARATUS FOR CULTURE, PROCESS FOR PREPARING APPARATUS FOR CULTURE, AND CULTURING METHOD

(75) Inventors: Masaharu Kojima, Ibaraki (JP); Tetsuji Sasaki, Ibaraki (JP); Takachika Azuma, Chiba (JP)

(73) Assignee: Kyokuto Pharmaceutical Industrial Co., Ltd., Tokyo (JP)

( * ) Notice: Subject to any disclaimer, the term of this patent is extended or adjusted under 35 U.S.C. 154(b) by 115 days.

(21) Appl. No.: 10/693,542

(22) Filed: Oct. 24, 2003

(65) Prior Publication Data

US 2005/0090005 A1      Apr. 28, 2005

(30) Foreign Application Priority Data

Oct. 28, 2002   (JP) ............................ 2002-311983

(51) Int. Cl.
*C12Q 1/24*      (2006.01)
(52) U.S. Cl. .................. 435/30; 435/287.4; 435/287.7; 435/288.1; 435/305.2; 435/305.3; 435/305.4; 435/305.1; 435/307.1; 435/309.1; 435/309.4
(58) Field of Classification Search ............. 435/288.3, 435/288.4, 305.1, 305.2, 305.3, 305.4, 307.1, 435/309.4
See application file for complete search history.

(56) References Cited

U.S. PATENT DOCUMENTS

| | | | |
|---|---|---|---|
| 3,631,575 A | | 1/1972 | Farris .......................... 85/599 |
| 3,907,647 A | * | 9/1975 | Sanderson ............... 435/305.1 |
| 4,054,490 A | * | 10/1977 | Vesterberg ................... 435/32 |
| 4,308,351 A | | 12/1981 | Leighton et al. ............ 435/284 |
| 4,686,190 A | | 8/1987 | Cramer et al. .............. 435/291 |

(Continued)

FOREIGN PATENT DOCUMENTS

| | | |
|---|---|---|
| EP | 0 590 513 A1 | 4/1994 |
| EP | 0 638 640 A2 | 2/1995 |
| FR | 2 819 523 | 7/2002 |

(Continued)

OTHER PUBLICATIONS

Patent Abstracts of Japan, Publication No. 06-296595, Publication Date Oct. 25, 2994, 2 pages.

(Continued)

*Primary Examiner*—David Redding
(74) *Attorney, Agent, or Firm*—Osha Liang LLP

(57) ABSTRACT

An apparatus for culture is provided, which apparatus enables to increase the ratio of a culture medium solution to the number of cells while keeping the density of the cells at a high level and diminishing the absolute number of the cells. The apparatus comprises a container having at least one concave part and at least one member (x) selected from the group consisting of a gelatinous material, a sponge material, and a mesh material, wherein the member (x) is placed within the concave part of the container, has at least one hollow by which a part or parts of a surface of the container in the concave part is bared, and holds a solution containing culture medium components.

Further, processes for preparing the apparatus, culturing methods that use the apparatus, a method for studying or observing an influence of a substance to be examined on cells or a piece of a tissue, a kit for making the apparatus, and a flat substrate for culture are provided.

According to the present invention, it becomes possible to culture cells or the like for a longer period of time under good conditions.

8 Claims, 18 Drawing Sheets
(4 of 18 Drawing Sheet(s) Filed in Color)

U.S. PATENT DOCUMENTS

| | | | |
|---|---|---|---|
| 5,023,173 A | 6/1991 | Horwitz et al. | 435/29 |
| 5,026,649 A | 6/1991 | Lyman et al. | 435/284 |
| 5,605,836 A * | 2/1997 | Chen et al. | 435/305.4 |
| 5,955,352 A * | 9/1999 | Inoue et al. | 435/287.7 |

FOREIGN PATENT DOCUMENTS

| | | |
|---|---|---|
| GB | 2 233 760 A | 1/1991 |
| JP | 6-44860 | 6/1994 |
| JP | 6-296595 | 10/1994 |
| JP | 7-46988 | 5/1995 |
| JP | 7-97982 | 10/1995 |
| JP | 8-62209 | 3/1996 |
| JP | 2619885 | 3/1997 |
| WO | WO 91/06624 | 5/1991 |

OTHER PUBLICATIONS

Patent Abstracts of Japan, Publication No. 08-062209, Publication Date Mar. 8, 1996, 2 pages.
John Paul, "Cell and Tissue Culture" Fourth Edition RePrint, Churchill Livingstone Edinburgh and London 1973, pp. 234-239.
R.G.H. Cotton et al., "Somatic Mutation and the Origin of Antibody Diversity. Clonal Variability of the Immunoglobulin Produced by MOPC 21 Cells in Culture" European Journal of Immunology, vol. 3, Mar. 1973, pp. 135-140.
European Search Report dated Dec. 3, 2003, 3 pages.
Front page and legal status of WO 02/057405 A1, 2 pages.

* cited by examiner

Rate of dye's liberation from gel

Ratio of IL-2 that diffused to solution within hollow

Culture in hollows in agarose gel

Culture in wells of 96-wells plate

Compensation by hypoxantin for inhibition against cell proliferation by aminopterin (after four days' culture)

Compensation by hypoxantin for inhibition against cell proliferation by aminopterin (after six days' culture)

APPARATUS FOR CULTURE, PROCESS FOR PREPARING APPARATUS FOR CULTURE, AND CULTURING METHOD

TECHNICAL FIELD

The present invention relates to a substrate for culture and an apparatus for culture, which are useful for culturing cells and pieces of tissues of *Homo Sapiens* and other mammals, plants, insects, and the like. The present invention also relates to a process for preparing the apparatus for culture, a kit for making the apparatus for culture, a culturing method of cells or a piece of a tissue, and a method for studying or observing an influence of a substance to be examined on cells or a piece of a tissue.

The present invention is useful in the case where cells or a piece of a tissue are cultured in vitro for a clinical diagnostic test or in clinical and basic research fields. The present invention is especially useful in the case where an influence or a function of a medicine to be examined on cells or a piece of a tissue is studied or observed.

BACKGROUND

To culture cells in vitro, most of nutrients and growth factors that are necessary for culture should be artificially put into a culture medium solution. By taking in the nutrients and growth factors that are dissolved in the culture medium solution, cultured cells keep themselves alive, proliferate, and produce useful substances. During that time of period, the cells consume e.g., oxygen, nutrients, and growth factors, and excrete, e.g., carbon dioxide and waste matters including metabolites. In the case where cells are cultured for a long time of period, the amount of nutrients in a culture medium solution or oxygen in surroundings may become to be insufficient and thus the cells may become not to proliferate or exist.

By the way, when an influence of a medicine, a growth factor, an inhibitor, a regulator, a toxin, a unknown factor, a nutrient, a chemical, or the like on cells is studied, a relationship between, not the absolute amount of the medicine but the concentration of the medicine in a culture medium solution, and the influence of its presence on the cells, is studied. In this case there is a problem that, as a culturing time elapses, the concentration of the medicine in the culture medium solution lowers because the medicine is consumed, namely, the concentration of the medicine cannot be constantly maintained.

Conventionally, in the case where cells or a piece of a tissue are cultured for a long time of period and influences of a medicine on them are studied or observed by using, as a container for culture, a petri dish, a flask, a multi-well plate, or the like, in the beginning of the culture a small number of the cells or a small amount of a tissue is used and a large amount of a culture medium solution is put into the container for culture, or the culture medium solution is exchanged during the culture. Now, we explain more specifically about the latter case. Cells or a piece of a tissue should be studied or observed in a certain cell density or a certain amount of the tissue that is suitable for culture. Also, according to the cell density or the amount of the tissue, a suitable amount of the culture medium solution may be specified. Therefore, the culture experiment may be started by using a suitable amount of a culture medium solution containing a medicine to be examined in a predetermined concentration, and if the period of studying or observing the cells or the piece of the tissue is prolonged, it is necessary that all or part of the culture medium solution is exchanged with a fresh and same solution containing the medicine to be examined in the same, i.e., initial concentration.

Conventional methods, by which cells or a piece of a tissue (hereafter, "cells or the like") are cultured by using, as a container, a petri dish, a flask, a multi-well plate, or the like and by which the cells or the like are studied or observed for a long time of period, have the following defects:

(1) In some cases the culture should be started under such a condition that the number of cells or the amount of a tissue is small in a comparison with the amount of the culture medium solution, that is, the density of the cells or the like is low. That the cell density or the like is low usually means that the surroundings or environment for proliferation are poor. Therefore, the start of the logarithmic growth phase lags, in other words, the preparatory period for proliferation becomes long.

(2) If a large amount of a culture medium solution is used in a container (this is useful to minimize a fluctuation of a concentration of a medicine to be examined), the level of the culture medium solution becomes high. In this case an efficiency of exchange of gases such as oxygen and carbon dioxide in the bottom (where the cells adhere) of the container for culture is low, namely, culturing conditions are poor.

(3) During an exchange of a culture medium solution, it is necessary to conduct an additional axenic manipulation, a risk of contamination is increased, it is difficult to hold the amount of the culture medium solution to be constant after its exchange, and the cells and the like tend to move from their original positions to other positions after the exchange of the culture medium solution, except that cells have a property that they adhere or stick tight to a container. Therefore, exchange of the culture medium solution during culture is disadvantageous to study or observe the same cells continuously.

Now, we more specifically explain the above defect 1. In a logarithmic growth phase, the time that the number of cells becomes twice the original number of them by their fissions is constant. Therefore, until, e.g., contact inhibition arises, the number of cells becomes $2^n$ after the above-mentioned constant time runs n-times. If the contact inhibition and the like does not arise, the cells continuously proliferate while, in some cases, layering to each other as long as good conditions are maintained about nutrients, oxygen, waste matters, and the like. If an influence of a medicine or the like on cells is studied during the logarithmic growth phase, the influence can be readily recognized. However, if the cell density is low in a culture medium solution or if culturing conditions such as medium components differ from those in preliminary culture, usually cells do not come to a logarithmic growth phase right after culture is started, although it depends on the kind and character of cells. Further, if the cell density is low, it takes a longer time of period to change culture surroundings to be convenient for proliferation of cells by producing growth factors and the like by which the cells are up-regulated. For conditioning the surroundings, it is advantageous that the same kind of cells are nearby gathered, but there are disadvantageous that the number of cells is too small and that the cells are sparse. Because of the reasons stated above, the leading or warm-up time, i.e., a period until a study of an influence of a medicine can be started, becomes longer.

Therefore, for example, when myeloma cells that proliferate rapidly are cultured for a relatively long period of time, i.e., for five days or longer, and with the lapse of time an influence of a medicine on the myeloma cells is studied, a method wherein a large amount of a culture medium solution is used, a method wherein a small number of cells is innoculated, or both are usually conducted. However, when these methods are conducted, the cell density becomes low. If one tries to study or observe states of cells under a condition that the cell density is low, only a few number of cells can be observed in a view field of a microscope under a magnification that the states of cells can be checked. Thus, one can not efficiently observe the cells. If the cell density is adequate for observation at the beginning of culture, in other words, if culture is started under a condition that the cell density is high, it is difficult to study or observe with the lapse of time the influences of a medicine to be examined, a nutrient, or the like on the cells for a long period of time without exchange of the culture medium solution. This is because the medicine to be examined, nutrient, or the like in the culture medium solution is rapidly consumed.

There are some apparatuses by which cell density can be locally increased to some extent. For example, in round (U-shape) bottomed or V-shape bottomed micro-titer plates, cells can be concentrated near the center bottom of wells. This is because the cells are settled down by their gravity. Thus, one can start to culture the cells at a high cell density locally with relatively a larger amount of a culture medium solution. However, the use of the round (U-shape) bottomed or V-shape bottomed micro-titer plates have following defects:

(1) The cells may excessively contact to each other. Thus, it is difficult to use the plates to culture cells that suffer contact inhibition.

(2) The cells may make laminated layers. For observing the cells by using a microscope, it is inconvenient if they exist in different vertical positions. For observing the cells during their culture, they are better that the bottom of a well or a container is substantially flat in horizontal direction (e.g., flat bottom or C-shape bottom) and that the cells exist as a monolayer.

(3) When cells become a multiple layer, oxygen, nutrients, etc., may come short in the lower layer.

(4) If a micro-titer plate is used, the amount of a culture medium solution in a well may not be increased. Even if the well is filled with the culture medium solution, its amount is, e.g., 0.3 milliliter, and would still be small to culture cells for a long time of period. Thus, in the course of culture, the solution should be exchanged. However, when the solution is exchanged, the cells may disperse. To avoid the exchange of the culture medium solution, a micro-titer plate having deep wells may be used. However, if the deep well is filled with the culture medium solution, the depth of it is increased. In this case, the culturing conditions would become poor. For example, oxygen will become short at the bottom where cells exist. This is because oxygen derived from air phase difficultly reaches to the bottom.

(5) To condition the environment for proliferation, cells would produce up-regulating factors and the like. If the volume of the culture medium solution is simply increased, the factors would quickly diffuse or spread in the culture medium solution. Namely, the factors would be diluted. This is not preferable. It is better that the cell-produced up-regulating factors accumulate near the cells.

Followings are other known methods for culturing cells and the like in vitro. Namely, Japanese Patent Publication No. Hei. 06-44860 B discloses a method wherein a spinner bottle and an insert are used, at least of which insert is constituted by a cell-impermeable and liquid medium-permeable net or membrane, and culture is conducted while continuously exchanging a culture medium solution inside the insert for a culture medium solution outside the insert through the net or membrane. Japanese Patent Publication No. Hei. 07-97982 B discloses a method for obtaining a cell product by culturing cells for a long time of period outside hollow fibers while supplying nutrients and oxygen to the cells by circulating a culture medium solution in the hollow fibers. Japanese Patent No. 2619885 discloses a method wherein cells are trapped inside hollow fibers, substances that are essential to culture the cells are supplied by circulating a liquid such as a culture medium solution outside the hollow fibers, and metabolites that the cells secrete and that are dissolved in the liquid are isolated from the liquid. However, these methods were developed for the purpose of culturing a larger number of cells or simplifying the isolation of cells' metabolites or products. Thus, these methods are not suitable to study or observe states of cells with the lapse of time.

Apparatuses have also been proposed that are suitable to culture cells and to study states of the cells with the lapse of time. For example, an apparatus that is used by combining a tissue culture insert (Nalge Nunc International) with a multi dish (Nalge Nunc International) and other apparatus that is used by combining a cell culture insert (Becton Dickinson and Company) with a companion plate (Becton Dickinson and Company) are known. To these apparatuses the principle of the invention disclosed in U.S. Pat. No. 4,308,351, namely, a method wherein an apparatus comprising a well and an insert is used which insert comprises a permeable membrane in its upper part, and a tissue is cultured in the insert (i.e., under a permeable membrane), is applied.

Further, European Patent Publication Nos. 0638640 A2 and 0590513 A2 disclose apparatuses that are useful when an interaction between two kinds of cells is studied without physically contacting two groups of the cells to each other by separating the groups by a membrane. They were invented by developing the invention disclosed in U.S. Pat. No. 4,308,351. In the apparatuses disclosed in European Patent Publication Nos. 0638640 A2 and 0590513 A2, an insert is put into a culture vessel wherein the bottom of the insert is made of a microporous membrane through which cells can not pass. The cells are cultured on and below the membrane, namely, in two places which are within the culture vessel and within the insert. In these apparatuses, a culture medium solution is supplied to the inside of the insert through the membrane. Also, the culture medium solution can be exchanged after the insert is taken out from the vessel. Further, in the apparatus disclosed in European Patent Publication No. 0590513 A2, a culture medium solution can be exchanged through a pipette that has been inserted into the culture medium solution between an inner wall of the vessel and an outer wall of the insert. Therefore, when these apparatuses are used, it is not necessary to heighten the level of the culture medium solution so much. Further, these apparatuses have a structure that there is a space on and above the surface of the culture medium solution and that therefore an enough amount of gases can be supplied to the cells. By using these apparatuses, the states of the cells can also be studied by taking out the insert from the culture vessel.

Japanese Patent Publication No. Hei. 07-46988 B discloses a technique by which cells are cultured using a porous material that is holding a culture medium solution. Specifically, it discloses that a culture medium solution is held by a porous polyurethane foam (PUF) in which polyurethane molecules a matrix of a peptide such as collagen is made and that adhesive animal cells are adhered to the foam and are cultured. In this invention, the PUF has a form of a chip having a size of preferably 1 to 3 mm and plays as a carrier to which the cells are adhered. Nutrients and gases that are necessary to culture the cells are supplied from a culture medium solution inside a culture vessel, into which the PUF chips are put.

One example of materials that can be gelatinized is agar. As a method for culturing cells by using agar, a soft agar method has been known, which is used for cloning and was published about 30 years ago (please see R. G. H. Cotton, et. al., Eur. J. Immunol., 3, p.p. 135–140 (1973) and John Paul, Cell and Tissue Culture, 4th Ed., Churchill Livingstone Edinburgh and London, p.p. 234–239 (1973)). This method comprises seeding cells in an extremely low density in a culture medium solution containing agar in a low concentration and culturing in gelatinous soft agar cell colonies, each of which has proliferated from one cell. Also, in assays for blood stem cells or myeloid stem cells, colonies are formed in soft agar or methylcellulose or its derivative and are studied or observed.

Further, in experiments using cultured cells, electric potentials of the cells are often measured. Examples thereof include methods wherein electric potentials of cells are measured by contacting the cells with electrodes that are placed on a bottom of a container (please see Japanese Patent Early-publication Nos. Hei. 06-296595 and Hei. 08-62209). However, if the soft agar method is used in these methods, it becomes difficult to contact the cells with the electrodes. Thus, the soft agar method is disadvantageous for measuring electric potentials of cultured cells.

A method has been known wherein an electrical resistance that arises in epithelial cells when an electric current passes through mono-layered those cells is measured while culturing those cells without using the soft agar method. In that method, using an apparatus disclosed in U.S. Pat. No. 4,686,190, an electric current is passed through a layer that has been formed by fusing a support with cells that has been proliferated on the support.

SUMMARY

As explained above, many techniques have been proposed about cell culture in vitro. However, no apparatus for culture has been known, which enables to increase the ratio of a culture medium solution to the number of cells while keeping the density of the cells at a high level and diminishing the absolute number of the cells and by which cells can be observed. An apparatus for culture has been desired, in which the absolute amount of the culture medium solution can be increased when cells or the like are cultured. In the apparatus for culture of this type, the absolute amount of a nutrient, a medicine or the like that is to be examined can also be increased when it is contained in the culture medium solution. In this case, even if the nutrient is consumed or the medicine or the like is decomposed by metabolism in the course of culture, its concentration can be maintained in an error range within which the change of the concentrations scarcely give any effect. As a result, it becomes possible to culture cells or the like for a long period of time. Also, it becomes possible to study or observe an influence of a medicine to be examined on cells or the like for a long period of time.

Further, an apparatus for culture has been desired, by which apparatus everyone can readily culture cells or the like, and can study or observe an influence of a medicine or the like on the cells or the like under an identical condition by merely preparing a culture medium solution and the cells or the like.

Furthermore, it has been desired that electric or electrostatic potential of cells or the like can be determined during the study or observation of the cells or the like for a long period of time.

Additionally, to study or observe cells or the like for a prolonged period of time, it is preferable that an apparatus for culture is proposed, by which apparatus a culture medium solution can be readily taken out and added.

It is also preferable that an apparatus for culture is proposed, by which apparatus an influence of a medicine or the like to be examined on cells or the like can be readily studied or observed.

To develop an apparatus for culture that satisfies any or all of the above requirements, the present inventors have extremely studied. The present invention has been accomplished as a result of the study.

A first invention is an apparatus for culture comprising a container having at least one concave part and at least one member (x) selected from the group consisting of a gelatinous material, a sponge material, and a mesh material, wherein the member (x) is placed within the concave part of the container, has at least one hollow by which a part or parts of a surface of the container in the concave part is bared, and holds a solution containing culture medium components.

The first invention includes following embodiments (1) to (8) singly or in combination of two or more of them.

(1) The solution further comprises at least one substance to be examined.

(2) The container is a laboratory dish for culture or a multi-well plate.

(3) The member (x) is a gelatinous material that has made by gelatinizing an aqueous solution of at least one member selected from the group consisting of agar, an agarose, and a cellulose derivative.

(4) The substance to be examined is selected from the group consisting of a medicine, a nutrient, a growth factor, and an inhibitory factor.

(5) The hollow has a cylindrical, inverted circular truncated conic, prismatic, or inverted truncated pyramidal shape.

(6) The height or depth of the hollow is at least a quarter of a diameter or length of a diagonal of the bottom of the hollow where the surface of the container is bared.

(7) On the bared part of the surface of the container, an electrode is pasted or printed.

(8) The member (x) further has at least one member selected from the group consisting of a hole where the surface of the container in the concave part is not bared and a large hollow that has a volume larger than that of the hollow.

A second invention is a process for preparing an apparatus for culture comprising:

step (a) of placing within a concave part of a container an article that can cover a part of a surface of the container and has a certain height;

step (b) of pouring into the concave part a solution that contains culture medium components and that can be gelatinized; and step (c) of gelatinizing the solution.

The second invention includes following embodiments (1) to (4) singly or in combination of two or more of them.

(1) The solution further comprises at least one substance to be examined, e.g., a medicine, a nutrient, a growth factor, and an inhibitory factor.

(2) The process further comprises step (d) of removing the article wherein the step (d) is conducted after the step (c).

(3) The container used has an electrode that has been pasted or printed on the surface of the container in the concave part and in the step (a) the article is placed so that it covers at least a part of the electrode. The electrode may be pasted or printed on a part or whole of the surface of the container in a bottom of a hollow which is made by removing the article.

(4) The process further comprises step (e) of (i) holing a part of a layer that has been made by gelatinizing the solution to form a hole where a surface of the container in the concave part is not bared or (ii) hollowing a part of a layer that has been made by gelatinizing the solution to form a large hollow which has a volume larger than that of a hollow which is made by removing the article and by which a part of a surface of the container in the concave part is bared, wherein the step (e) is conducted after the step (c). Of course, the step (e) may comprise the steps (i) and (ii).

A third invention is a process for preparing an apparatus for culture comprising:

step (A) of making within a concave part of a container a layer of at least one member (x) selected from the group consisting of a gelatinous material, a sponge material, and a mesh material, wherein the member (x) holds a solution that contains culture medium components; and step (B) of hollowing a part of the layer so that a part of a surface of the container in the concave part is bared to form a hollow.

The third invention includes following embodiments (1) to (6) singly or in combination of two or more of them.

(1) The solution further comprises at least one substance to be examined.

(2) The container used has an electrode that has been pasted or printed on the surface of the container in a bottom of the hollow which is made by the step (B).

(3) The container used has an electrode that has been pasted or printed on the surface of the container in only a part of a bottom of the hollow which is made by the step (B) and in the step (B) the hollow is made by hollowing a part of the layer that has been made in the step (A) so that the electrode is bared.

(4) The process further comprises step (C) of (i) holing a part of the layer that has been made in the step (A) to form a hole where a surface of the container in the concave part is not bared or (ii) hollowing a part of the layer that has been made in the step (A) to form a large hollow which has a volume larger than that of the hollow which has been made in the step (B), wherein the step (C) is conducted after the step (A). Namely, the step (C) may be conducted between the steps (A) and (B) or after the step (B).

(5) The layer is composed of a sponge material and/or a mesh material, and the step (A) comprises impregnating the solution into the sponge material and/or the mesh material.

(6) The layer is composed of a sponge material and/or a mesh material, to which a substance to be examined has been adhered by vacuum-drying or freeze-drying, and the step (A) comprises impregnating the solution into the sponge material and/or the mesh material.

A fourth invention is a process for preparing an apparatus for culture comprising:

step (I) of making within a concave part of a container a layer of at least one member (x) selected from the group consisting of a gelatinous material, a sponge material, and a mesh material;

step (II) of hollowing a part of the layer so that a part of a surface of the container in the concave part is bared to form a hollow; and step (III) of impregnating a solution that contains culture medium components into the layer.

If the member (x) is a gelatinous material, by impregnating the solution into the layer of the gelatinous material, the liquid that has been contained in the layer of the gelatinous material is exchanged by the solution.

The solution may further comprises at least one substance to be examined. Or, the member (x) may holds at least one substance to be examined.

The fourth invention includes the following embodiments (a) and (b):

(a) a process for preparing an apparatus for culture comprising making within a concave part or parts of a container a layer or layers of at least one member selected from the group consisting of a gelatinous material, a sponge material, and a mesh material (step Ia), hollowing a part or parts of the layer or layers that has been made in the step Ia so that a part or parts of a surface of the container in the concave part or parts is bared to form one or more hollows (step IIa), and having the layer that is composed of at least one member selected from the group consisting of a gelatinous material, a sponge material, and a mesh material holding a solution that contains culture medium components (step IIIa); and (b) a process for preparing an apparatus for culture comprising making within a concave part or parts of a container a layer or layers of at least one member selected from the group consisting of a gelatinous material, a sponge material, and a mesh material (step Ib) wherein the member holds at least one substance to be examined, hollowing a part or parts of the layer or layers that has been made in the step Ib so that a part or parts of a surface of the container in the concave part or parts is bared to form one or more hollows (step IIb), and having the layer or layers that is composed of at least one member selected from the group consisting of a gelatinous material, a sponge material, and a mesh material holding a solution that contains culture medium components (step IIIb).

A fifth invention is a process for preparing an apparatus for culture comprising:

step (1) of making a hollow in a layered sponge or mesh material;

step (2) of placing the layered sponge or mesh material in a concave part of a container; and step (3) of impregnating a solution that contains culture medium components into the layered sponge or mesh material.

Of course, the layered material may be composed of both a sponge material and a mesh material. The solution may further comprises at least one substance to be examined. Or, the layered sponge or mesh material may hold at least one substance to be examined.

The fifth invention includes the following embodiments (a) and (b):

(a) a process for preparing an apparatus for culture comprising making one or more hollows in a layered sponge material and/or mesh material (step 1a), putting the layered sponge material and/or mesh material that has been made in the step 1$a$ and that has one or more hollows into a concave part or parts of a container (step 2$a$), and having the layered sponge material and/or mesh material holding a solution that contains culture medium components (step 3$a$); and (b) a process for preparing an apparatus for culture comprising making one or more hollows in a layered sponge material and/or mesh material wherein the material holds at least one substance to be examined (step 1b), putting the layered sponge material and/or mesh material that has been made in the step 1b and that has one or more hollows into a concave part or parts of a container (step 2b), and having the layered sponge material and/or mesh material holding a solution that contains culture medium components (step 3b).

A sixth invention is a culturing method comprising 1) preparing an apparatus for culture of the first invention, 2) putting a culture medium solution and cells or a piece of a tissue to be examined into a hollow or hollows of the apparatus, and 3) culturing the cells or the piece of the tissue by incubating the apparatus.

A seventh invention is a culturing method comprising 1) preparing an apparatus for culture of the first invention with the proviso that the solution containing culture medium components also comprises at least one substance to be examined and that the member (x) further has at least one member selected from the group consisting of a hole where the surface of the container in the concave part is not bared and a large hollow that has a volume larger than that of the hollow in the apparatus, 2) putting a culture medium solution comprising the substance to be examined and cells or a piece of a tissue to be examined into the at least one hollow of the apparatus, 3) putting the same solution into the hole and/or the large hollow of the apparatus, and 4) culturing the cells or the piece of the tissue by incubating the apparatus, while, at need, supplying the substance to be examined by exchanging the solution in the hole and/or the large hollow.

An eighth invention is a method for studying or observing an influence of a substance to be examined on cells or a piece of a tissue comprising 1) preparing an apparatus for culture of the first invention with the proviso that the solution containing culture medium components comprises no substance to be examined, 2) putting the same solution and the cells or the piece of the tissue to be examined into the at least one hollow of the apparatus, 3) culturing the cells or the piece of the tissue by incubating the apparatus, 4) putting the substance to be examined into the at least one hollow during the culture, and 5) studying or observing the influence of the substance to be examined on the cells or the piece of the tissue.

A ninth invention is a kit for making an apparatus for culture comprising a container having at least one concave part, culture medium components, a substance of which aqueous solution can be gelatinized, and (i) at least one article that can cover a part of a surface of the container in the concave part and has a certain height or (ii) a tool for hollowing a part of a layered gelatinous material which is made by gelatinizing an aqueous solution of the substance.

The ninth invention include the following embodiments (i) and (ii):
(i) a kit for making an apparatus for culture comprising a container having a concave part or parts, culture medium components, a substance of which aqueous solution comes to be a gelatinous material, and at least one article that can cover a part or parts of a surface of the container in the concave part or parts and has a certain height; and
(ii) a kit for making an apparatus for culture comprising a container having a concave part or parts, culture medium components, a substance of which aqueous solution comes to be a gelatinous material, and a tool for hollowing a part or parts of a layer or layers of the gelatinous material.

A tenth invention is a flat substrate for culture, which is made of a sponge or mesh material, which has a hollow, and within which culture medium components or at least one substance to be examined are held.

The flat substrate may be made of both a sponge material and a mesh material. Within the flat substrate, culture medium components and at least one substance to be examined may be held. The flat substrate may further have a hole, a large hollow which has a volume larger than that of the hollow, or both.

The tenth invention includes the following embodiments (i), (ii), and (iii):
(i) a flat substrate for culture, which is made of a sponge material and/or a mesh material, which has one or more hollows, and within which culture medium components are held;
(ii) a flat substrate for culture, which is made of a sponge material and/or a mesh material, which has one or more hollows, and within which at least one substance to be examined is held; and
(iii) a flat substrate for culture, which is made of a sponge material and/or a mesh material, which has one or more hollows, and within which culture medium components and at least one substance to be examined are held.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A is a plane view, FIG. 1B is a cross sectional view, and FIG. 1C is a perspective view.

FIG. 2A is a plane view, FIG. 2B is a cross sectional view, and FIG. 2C is a perspective view.

FIG. 3A is a plane view and FIG. 3B is a cross sectional view.

FIG. 4A is a plane view and FIG. 4B is a cross sectional view.

FIG. 5A is a plane view and FIG. 5B is a cross sectional view.

DETAILED DESCRIPTION

Hereafter the present invention will be explained with reference to preferable embodiments.

First, we explain meanings of some terms that are used in this specification with making reference to drawings at need.

A "container" is one that is used to support the member (x).

Figure 4A:
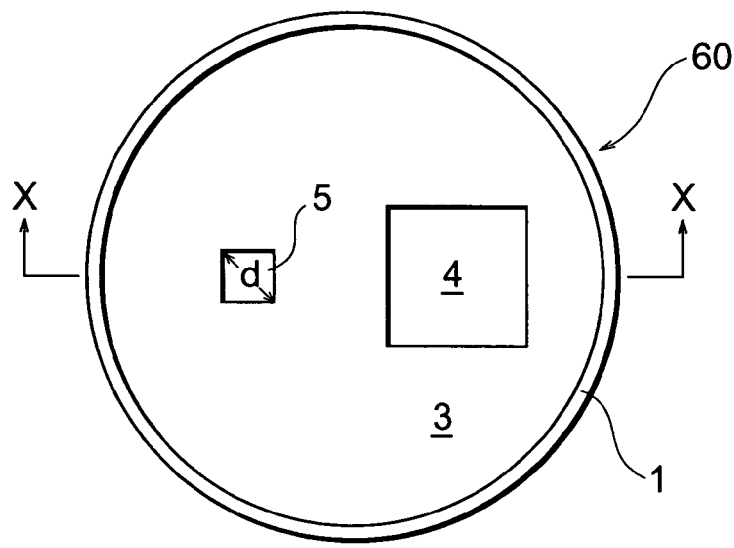
FIGS. 4A and 4B show a preferable example of the apparatus for culture having a large hollow of the present invention.
Figure 4B:
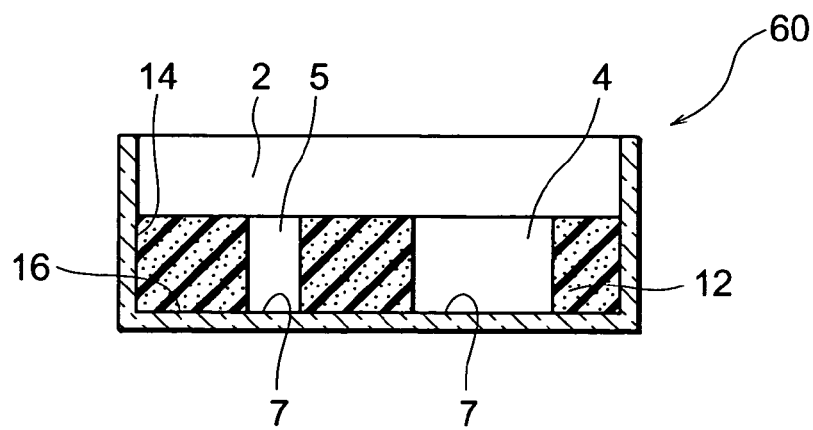
Figure 5A:
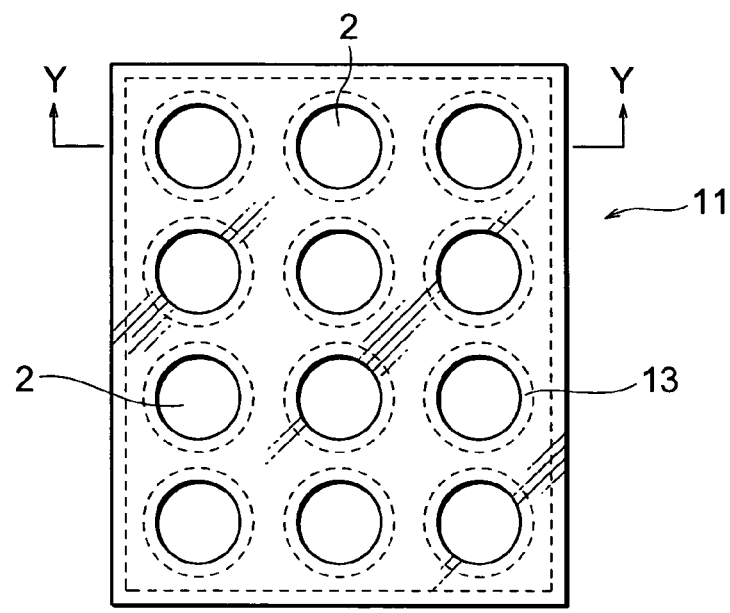
FIGS. 5A and 5B show a 12-well plate that may be used as a container in the present invention.
Figure 5B:
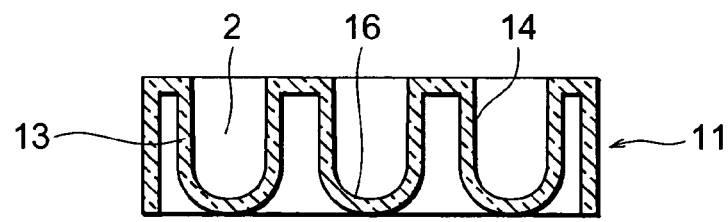
Figure 5C:
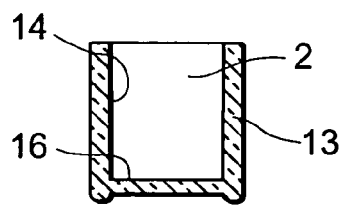
FIGS. 5C and 5D show examples of shapes of wells of a multi-well plate by cross sectional views.
Figure 5D:
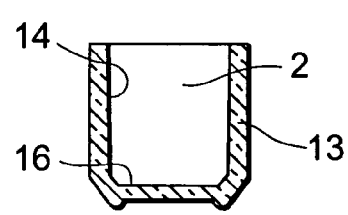
Figure 6:
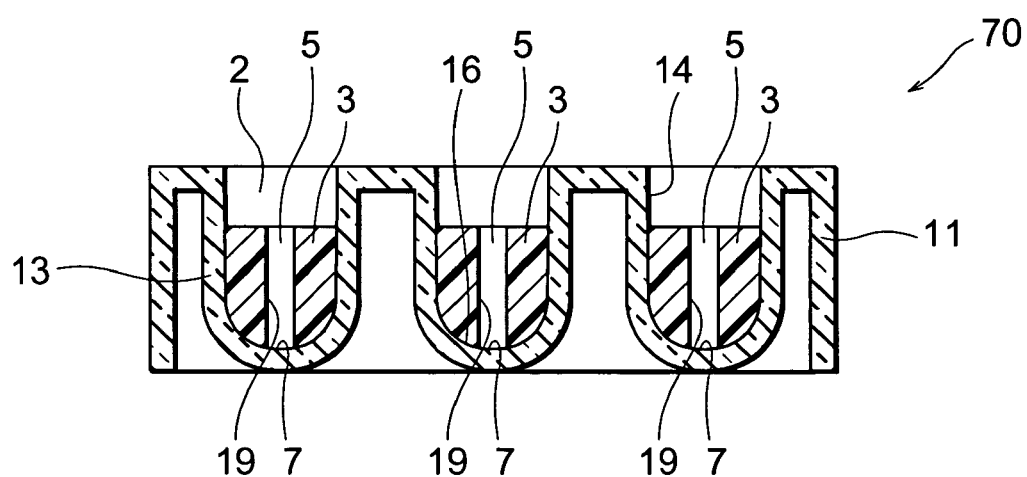
FIG. 6 show another preferable example of the apparatus for culture of the present invention by cross sectional view.

A "concave part" is, in other word, a hollow part. A surface of a concave part is, namely, a surface of a container in the concave part. As shown in FIGS. 1A to 4B if the container is a laboratory dish 1, the concave part 2 is an inside of the dish 1, and a surface of the concave part includes surfaces 14, 16 of an inner side wall and a bottom of the dish 1. If the container is a multi-well plate 11, as shown in FIGS. 5A to 6, insides of the wells 13 are the concave parts 2. The shape of the concave part is not limited. For example, a well 13 that defines the shape of the concave part may have a bottom having a U-shape (a round bottom, see FIG. 5B), a flat shape (a flat bottom, see FIG. 5C), or a C-shape (a flat bottom having carved edge, see FIG. 5D).

As shown in FIGS. 1A to 6, a bottom 7 of a "hollow" 5 or "large hollow" 4 is also a part of a surface of a concave part 2, e.g., a part of a bottom surface 16 of a laboratory dish 1 or a well 13 of a multi-well plate 11. On the other hand, a bottom 17 of a "hole" 9 is a surface of the member (x). A side wall 19 of the "hollow" 5 or "large hollow" 4 or "hole" 9 is also a surface of the member (x).

Now, the apparatus for culture according to the first invention will be explained with making reference to drawings at need.

Figure 1A:
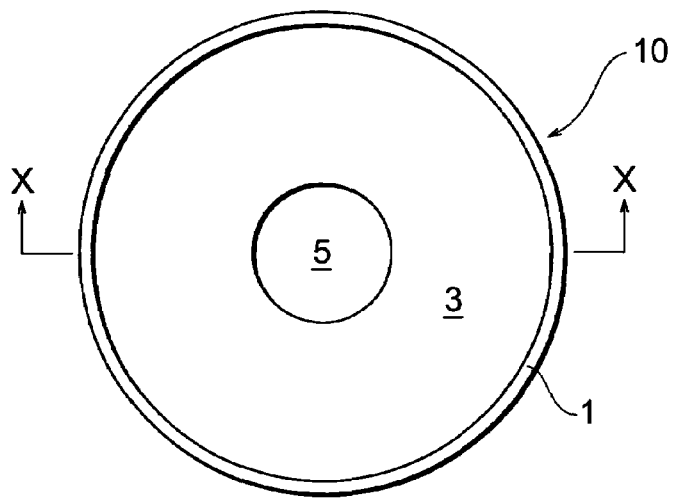
FIGS. 1A, 1B, and 1C show a preferable example of the apparatus for culture of the present invention.
Figure 1B:
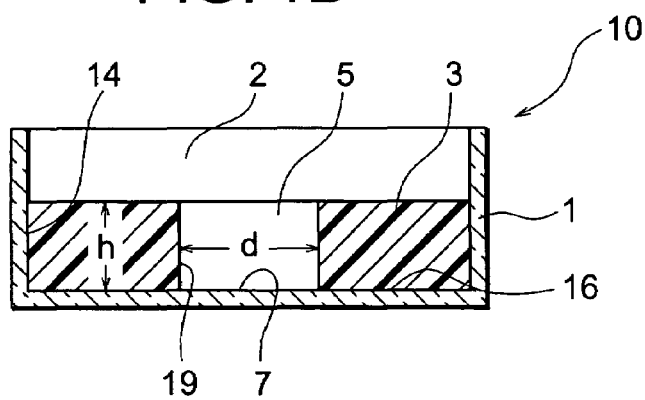
Figure 1C:
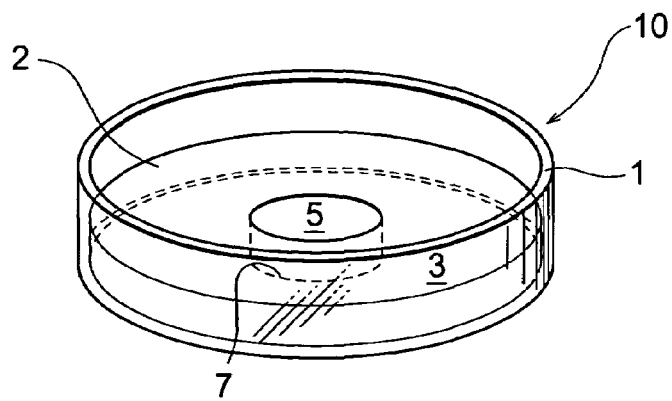
Figure 2A:
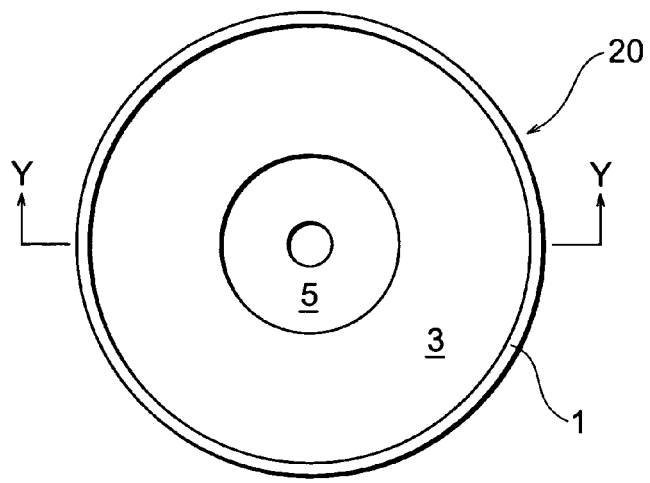
FIGS. 2A, 2B, and 2C show another preferable example of the apparatus for culture of the present invention.
Figure 2B:
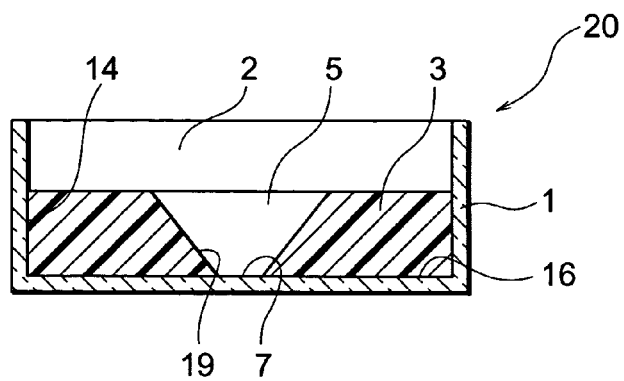
Figure 2C:
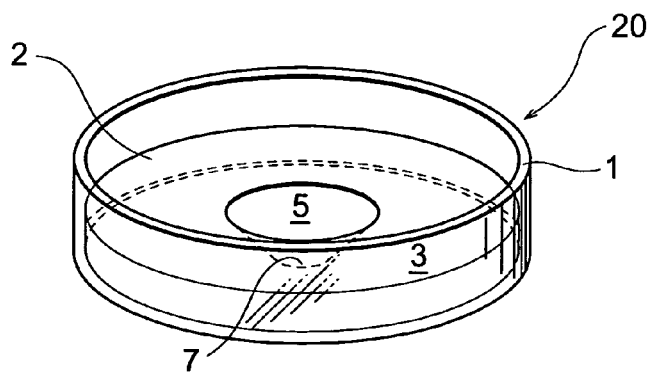

FIGS. 1A, 1B, and 1C show a preferable example of the apparatus for culture of the first invention. FIG. 1A is a plane view, FIG. 1B is a cross sectional view taken along lines X—X in FIG. 1A, and FIG. 1C is a perspective view. FIGS. 2A, 2B, and 2C show another preferable example of the apparatus for culture of the first invention. FIG. 2A is a plane view, FIG. 2B is a cross sectional view taken along lines Y—Y in FIG. 2A, and FIG. 2C is a perspective view.

Apparatuses 10, 20 for culture comprise a laboratory dish 1 and a gelatinous material 3. The laboratory dish 1 is a container having a concave part 2 and is used to support the gelatinous material 3. The gelatinous material 3 is placed in the laboratory dish 1. The gelatinous material 3 has a hollow 5 that pierces through the layer of the gelatinous material 3. In the portion where the hollow 5 is made, a part of the bottom surface 16 of the laboratory dish 1 is bared. The part is also a bottom surface 7 of the hollow 5. The gelatinous material 3 holds a solution that contains culture medium components.

The container is not limited to the laboratory dish 1, as long as it has at least one concave part and has hardness such that it can hold its shape by itself. Preferable examples of the container include a laboratory dish (e.g., a laboratory dish for culture) that is shown in FIGS. 1A to 4B and has one concave part 2, and a multi-well plate that has two or more concave parts as shown in, e.g., FIGS. 5A to 6. For example, one comprising a cylindrical laboratory dish and a rectangular or square plate made of a plastic resin in which the dish is placed on the plate (see FIGS. 7 and 8), a culture flask, and a laboratory dish or a multi-well plate of which the inner bottom(s) has corners can also be used as the container.

The material of the container is not limited as long as it has hardness such that the container can hold its shape by itself. Preferable examples of the material include transparent plastics and glass. Ceramics, surface-treated papers, and some plants such as bamboo can also be used as the materials for the container. However, it is preferable that at least a part that corresponds to a hollow, i.e., a part where cells or the like are concentrated, is transparent or comprises transparent parts in a large ratio for studying or observing the cells or the like.

The inner surface of the container that faces the concave part, namely, the surface of the concave part, may be hydrophilic or hydrophobic. However, when cells are cultured, it is preferably hydrophilic in some extent. The inner surface of the container may be treated to make it more hydrophilic.

The gelatinous material that is placed in the container is one that can be a gel under culturing temperatures, does not allow cells to pass through, and allows medicines, sugar, proteins, amino acids, vitamins and the like to pass through.

In the apparatus for culture according to the first invention of the present invention, the gelatinous material holds a solution that contains culture medium components. Namely, it holds at least culture medium components and a liquid that dissolves the components. The liquid is usually water or a buffer. The culture medium components are a mixture of components of a culture medium solution or culture medium that is used to culture a specific or general cell or tissue. The culture medium solution or culture medium is composed of the liquid and culture medium components. In the apparatus for culture according to the first invention of the present invention, waste matters such as cell metabolites diffuse from the culture medium solution in the hollow into the solution that is held by the gel. Thus, the concentration of the waste matters in the culture medium solution lowers.

In one embodiment of the apparatus for culture according to the first invention of the present invention, the solution that is held by the gelatinous material may further comprise at least one substance to be examined. In this type of an apparatus, the substance to be examined, e.g., a medicine, a sugar, a nutrient such as a protein, an amino acid or a vitamin, a growth factor, an inhibitor, a toxin, a chemical, or an other known or unknown factor is supplied by a diffusion to the culture medium solution in the hollow from the gelatinous material, more specifically, from the culture medium solution that is held by the gelatinous material.

Examples of substances that compose the gelatinous material, namely, that become the gelatinous material with a liquid such as water, include agar, agarose, cellulose, cellulose derivatives such as methyl cellulose, carboxymethyl cellulose, and hydroxyethyl cellulose, dextran, Sepharose™ (cross-linked agarose), acrylamide, pectin, mannan, gelatin, starch, alginic acid, porphyran, hyaluronic acid, chitosan, poly-L-leucine, locust bean gum, Carrageenan, xanthan gum, galactomannan, and fibrin derived from fibrinogen. These substances can be used singly or as a mixture of two or more of them. Agar and agarose are especially preferred because they can hold under cultural temperatures the shape of the hollow in a relatively long period of time and are inexpensive. When a substance such as acrylamide that becomes a gel with a liquid by polymerization is used, the gel should be sufficiently washed before its use to remove monomers that have not been polymerized, a polymerization initiator, a polymerization promoter, and the like. This is because these materials may show any cytotoxity.

The concentration of the substance that composes the gelatinous material affects the size of the sieve of the gel. Therefore, if the solution that is held by the gelatinous material also comprises a substance to be examined, it is necessary to select the concentration of the substance that composes the gelatinous material according to the kind of the substance to be examined when the gelatinous material is prepared. If a substance to be examined has a low molecular weight, the concentration of agarose as a substance that composes the gelatinous material may be 0.5 to 1% in the agarose solution. However, its concentration is not limited within this range. Heightening the molecular weight of the substance to be examined brings passing or diffusion of the substance within a gel to be difficult. In this case, it is necessary to make a gel under a condition that the concentration of the substance that composes the gelatinous material is low. Namely, the size of the gel sieve should be enlarged. However, also in this case, a gel having a hardness such that shape of a hollow may be held should be made.

The degrees of cross-linking and branching of the substance that composes the gelatinous material also affect the size of the sieve of the gel. Thus, depending on the molecular weight of the substance to be examined, the degrees of cross-linking and branching of it should also be appropriately selected.

When agar is used as a substance that composes the gelatinous material, its purity should be noted. This is because lowering the purity brings the fluidity of the gel under a specific temperature to be high and finally the gel becomes to be unable to hold its shape. Therefore, when agar having an extremely low purity, it should be used in a higher concentration, comparing with the case where a purified agarose is used. Also in cases where other substances are used, the hardness of a gel should be adjusted by regulating the concentration of the substance that composes the gelatinous material or by using two or more substances and regulating the ratio between or among those substances.

In the apparatus for culture according to the first invention, instead of or together with the gelatinous material, a sponge material or a mesh material can be used. Namely, at least one member (x) selected from the group consisting of a gelatinous material, a sponge material, and a mesh material can be used. Examples of the sponge material include cellulose sponge, collagen sponge, and a sponge of acrylamide. In the first invention, various sponge materials and mesh materials can be used as long as waste matters such as cell metabolites and substances to be examined such as medicines and nutrients can pass through or diffuse in those materials. Further, as the member (x), e.g., a combination of a cylindrical thin mesh and a gelatinous material that is applied to the mesh can be used.

For example, in an embodiment that a gelatinous material exists only in a part of voids or vacancies of a mesh material, the substance to be examined can slowly diffuse and go into a medium solution in a hollow. Namely, sustained release of the substance to be examined can be attained.

In the apparatus for culture according to the first invention, the layer of at least one member (x) has one or more hollows by which part(s) of the inner bottom surface(s) of the container are bared. For example, the container is a laboratory dish for culture, a hollow or a plural number of hollows may be made. The shape of the hollow is not specifically limited. Preferable examples of the shape include a cylinder (see FIGS. 1A, 1B, and 1C), an inverted circular truncated cone (see FIGS. 2A, 2B, and 2C), a tetraangular prism (see FIGS. 4a and 4B), and an inverted truncated pyramid. A cylindrical shape and an inverted circular truncated conic shape are especially preferred.

The hollow is made so that it has a size which is appropriate to study or observe cells or the like and such that the cell density or the amount of a piece of a tissue becomes to be a value that is appropriate for culture. If the volume of the hollow is too large, e.g., the volume of the hollow is a half or more of the volume of the layer (including the volume of the hollow) of at least one member (x), absolute number of cells or absolute amount of a tissue that are put into the hollow should be enlarged to some extent. This case is not quite advantageous for culture for a long time of period. On the other hand, if the volume of the hollow is too small, number of cells or an amount of a tissue that can be put into the hollow and the time period that the cells or tissue can be proliferated are restricted. In this case, when the cells or the like are put into the hollow, the handling may also be difficult. In view of culture of the cells or the like, it is advantageous that the area of the bottom of the hollow is small to some extent because the cells or the like are concentrated.

Considering the easiness of putting the cells or the like into the hollow and that of study or observation of them, it is better that the volume of the hollow is such that the diameter of the bottom of it is in the range of about 4 to 8 mm. The depth of the hollow, namely, the height (mark h in FIG. 1B) of the layer of at least one member (x) is preferably not less than a quarter of the length of the diameter (mark d in FIG. 1B) or the diagonal in the bottom of the hollow (mark d in FIG. 4A). In this case, the lateral area of the hollow is not smaller than the area of the bottom of it. When the hollow is cylindrical and the height of the layer of at least one member (x) is a quarter of the diameter of the bottom of the hollow, the lateral area is the same as the bottom area. By enlarging the height of the layer of at least one member (x) while lessening the diameter of the bottom of the hollow, the ratio of the lateral area to the bottom area becomes large. If the diameter is the same as the height, the lateral area is four times larger than the bottom area. If the height is twice the diameter, the lateral area is eight times larger than the bottom area.

The volume of the hollow into which cells or the like are put is preferably 1/3 to 1/300, more preferably 1/10 to 1/100 of the volume of the layer (including the volume of the hollow) of at least one member (x) in view of the diffusions of substances to be examined such as medicines and nutrients and waste matters that cells or the like evacuate from a culture medium solution in the hollow to the solution that is held by the gelatinous material and the like, and in view of the passes of them within the gelatinous material and the like. However, it is not limited within this range.

The substance to be examined means a substance of which influences against cells or the like are intended to be examined. Examples of the substance to be examined include medicines, nutrients, growth factors, and inhibitory factors. In the present invention, various substances may be used as the substance to be examined, as long as they can dissolve in a medium solution, and can diffuse within at least one member (x) (i.e., can diffuse in spaces or room among substances that compose the member (x) or in areas where a liquid exists) and can transfer to or put in a culture medium solution in a hollow. Specific examples of the substance to be examined include biologically active substances (e.g., antibiotics including carcinostatics, function-activating substances such as growth factors, differentiation-inducing factors, apoptosis-inducing substances, and environmental hormones, and function-repressing substances) and their candidates, in addition to clinical remedies, generic chemicals, toxicants, poisons, venom, and deadly poisons.

Figure 3A:
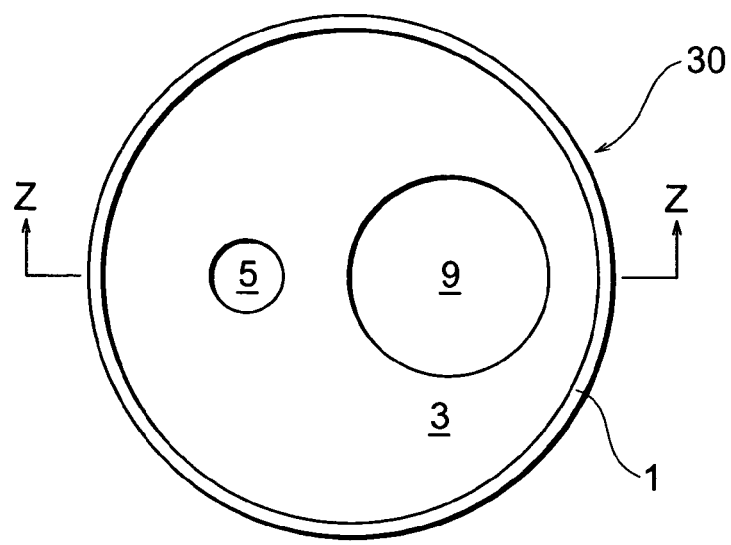
FIGS. 3A and 3B show a preferable example of the apparatus for culture having a hole of the present invention.
Figure 3B:
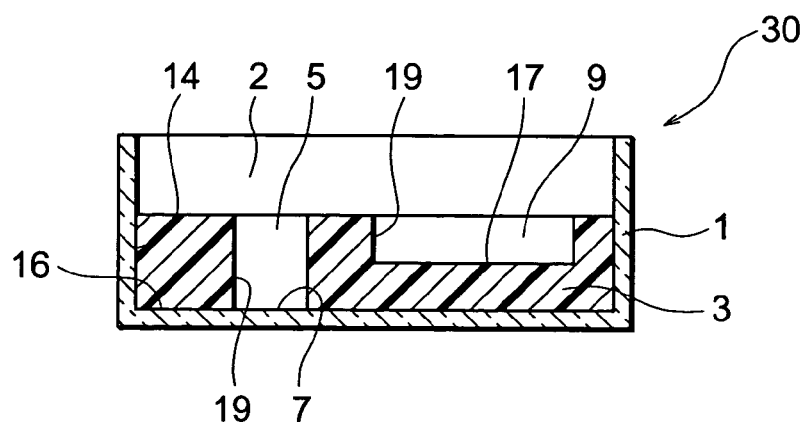

As shown in FIGS. 3A and 3B, in the layer of a gelatinous material 3 of the apparatus 30 for culture according to the first invention, hole 9 that does not bare the inner bottom surface 16 of the laboratory dish 1 as a container may be made in addition to the hollow 5. Alternatively, instead of or in addition to a hole, a large hollow may be made. In an embodiment of the apparatus 60 for culture according to the first invention that is shown in FIGS. 4a and 4B, a sponge material 12 has a hollow 5 and a large hollow 4 that bare parts of the inner bottom surface 16 of the laboratory dish 1. The large hollow 4 has a volume larger than that of the hollow 5 that is made in the member (x) and is used to culture cells or the like.

When cells or the like are intended to be cultured for a long period of time, the culture medium solution can be exchanged or the substance to be examined can be supplied by using these hole and/or large hollow. In this case, cells or the like can be cultured for a long period of time with a position of the cells or the like being scarcely moved when the culture medium solution is exchanged or the substance to be examined is supplied or supplemented.

The number of holes or large hollows is not specifically limited. The total volume of the holes and/or large hollows are preferably between about a half and a third of the volume of the layer (including the volumes of the hollow, hole and large hollow) of the member (x). However, it is not limited within this range. The layer may exist just around a hollow as long as it can maintain its shape by itself.

The shape of the hole or large hollow is not specifically limited. Examples of the shape include a cylinder, an inverted circular truncated cone, a tetraangular prism, and an inverted truncated pyramid. Also, the shape may be an indeterminate form or a shape like a quirk or trench (e.g., a trench having a shape like a doughnut that surrounds a hollow).

It is also possible to use at least one hollow among plural hollows as those that function as the hole or large hollow explained above. Namely, cells or the like are not put into at least one hollow among plural hollows that are made in the layer of the member (x), and the hollow(s) into which cells or the like are not put can also be used as a place for, e.g., exchanging a medium solution.

Figure 7:
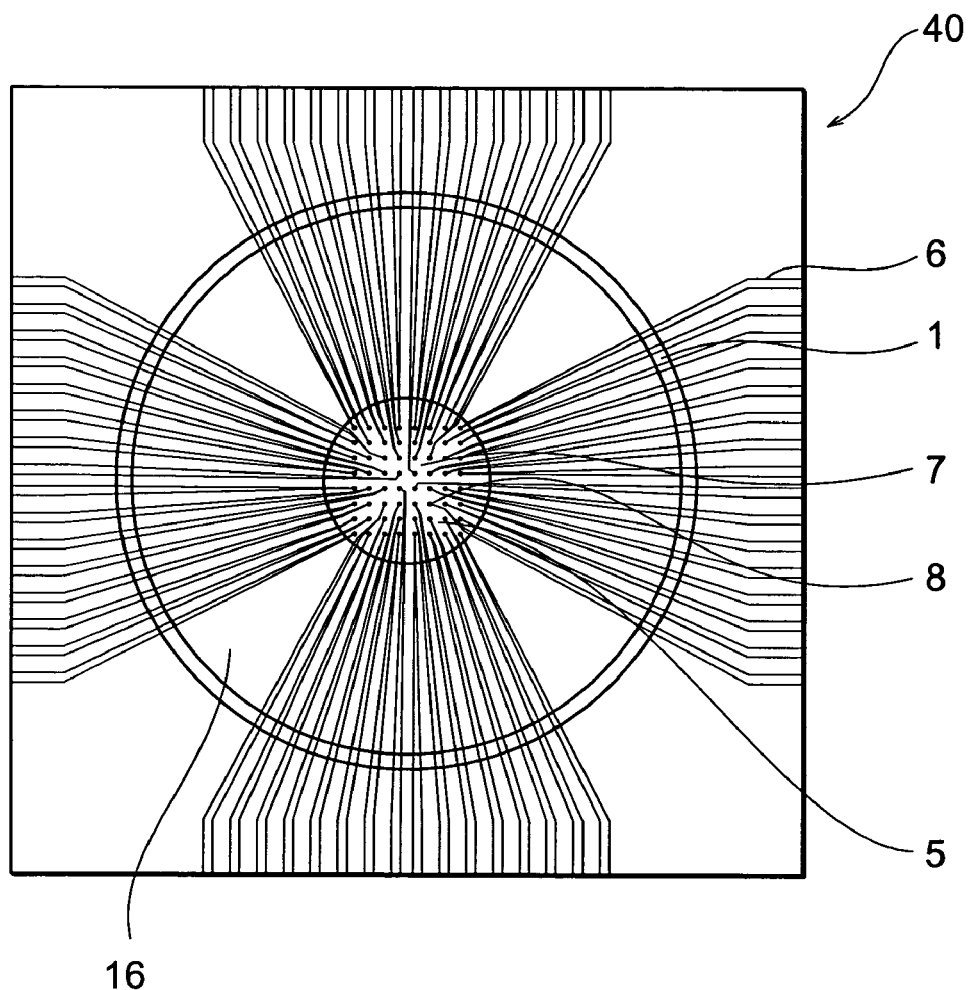
FIG. 7 is a plane view of an example of the apparatus for culture of the present invention in which on a bottom surface of the container in the concave part an electrode is pasted or printed.
Figure 8:
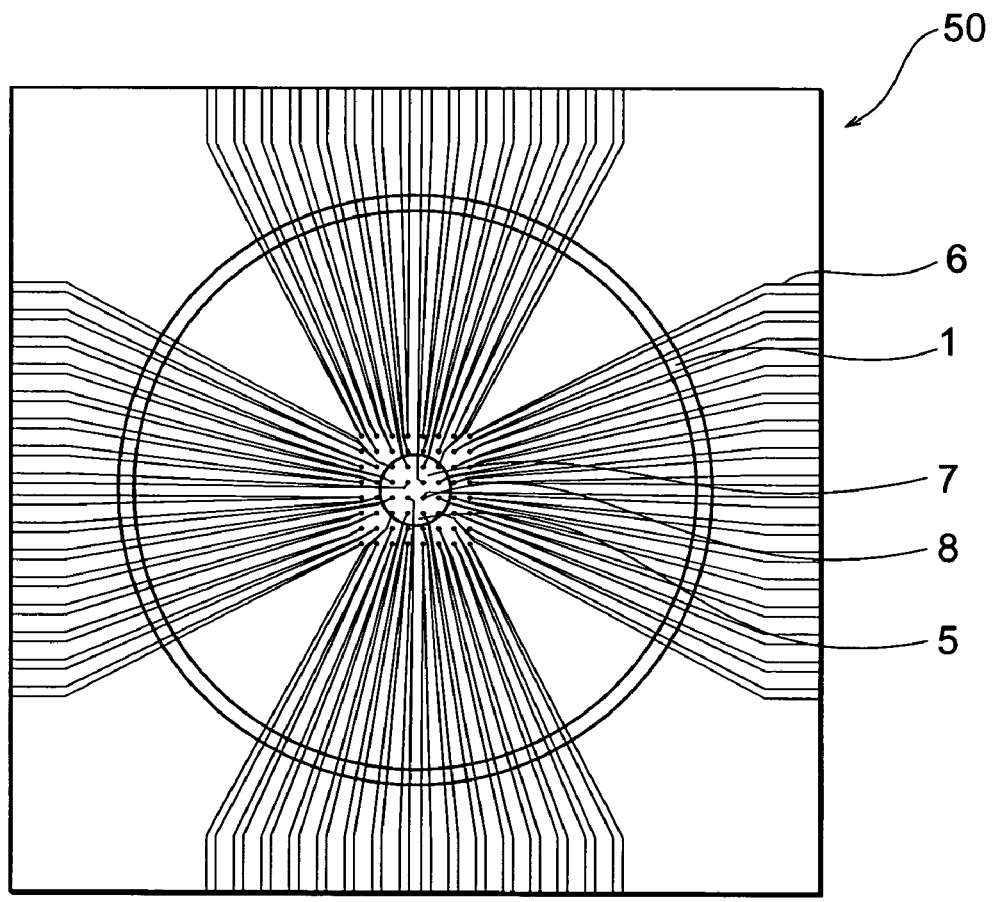
FIG. 8 is a plane view of another example of the apparatus for culture of the present invention in which on a bottom surface of the container in the concave part an electrode is pasted or printed.

If it is intended to determine electric potential of cultured cells, apparatuses 40 and 50 for culture that are shown in FIGS. 7 and 8 may be used in which electrodes 8 and leads 6 are pasted or printed on parts of the inner bottom surface 16 of the laboratory dish 1 as a support container and in which the electrodes 8 are set at the bottom 7 of the hollow 5. In the example that is shown in FIG. 7, electrodes 8 exist only a part of the bottom 7 of the hollow 5. In the example that is shown in FIG. 8, electrodes 8 exist all over the bottom 7 of the hollow 5.

The apparatus for culture according to the first invention is preferably made by one of methods according to the second to fifth inventions.

According to the second invention, to prepare an apparatus for culture according to the first invention provided that the member (x) is a gelatinous material, first, step (a) is conducted. Namely, an article that is used to make a hollow, that can cover a part of an inner bottom surface of a container, and that has a certain height is placed within a concave part of the container. In other words, the article is put on an inner bottom surface of, e.g., a laboratory dish or a well of a multi-well plate.

The article is used to make a hollow. Namely, by removing the article after the solution was gelatinized, a hollow can be formed. Thus, the shape and the size of the article corresponds to those of the hollow to be made. The certain height means a height such that the article can be taken out after the gelatinous material was made. Usually, the height is larger than that of the layer of the gelatinous material. However, if the article has a string or the like for taking out the article from the layer of the gelatinous material, the height may be about the same as that of the layer of the gelatinous material.

The article can cover a part or parts of the inner bottom surface of the container. The article may further have a part that occupies a space above the inner bottom surface of the container (i.e., a part corresponding to a hole) although the part of the article does not directly cover the inner bottom surface of the container. By using this type of an article, the hollow and the hole can be made at once. Or, the article may have, as parts that directly cover parts of the inner bottom surface of the container, a part that corresponds to a hollow and another part that corresponds to a large hollow. By using this type of an article, the hollow and the large hollow can be made at once.

Next, as step (b), a sol or solution that contains culture medium components and that can be gelatinized in a later step is poured into a concave part of a container. The sol or solution comprises, in addition to a solvent such as water and culture medium components, a substance that comes to compose a gelatinous material, e.g., agar or agarose. The sol or solution may further comprise one or more substances to be examined.

The sol or solution may be prepared as follows.

A solution containing a substance that comes to compose a gelatinous material at a concentration that is twice the final concentration and a culture medium solution containing culture medium components at concentrations that are twice the final concentrations are each prepared. These solutions thus prepared are mixed to each other at a ratio of 1:1 at about 40° C. or a temperature above 40° C. If an apparatus for culture that is used to culture an insect cell and that is used at a temperature lower than 37° C. is intended to be prepared, depending on the type or concentration of the substance that comes to compose a gelatinous material the temperature at the mixing of the solutions may be still lower. If the sol or solution also comprises at least one substance to be examined, a culture medium solution containing culture medium components and the substance to be examined at concentrations that are twice the final concentrations is prepared and then this culture medium solution is mixed with, at a ratio of 1:1, a solution containing a substance that comes to compose a gelatinous material at a concentration that is twice the final concentration. Or, a culture medium solution containing a substance that comes to compose a gelatinous material at a concentration that is twice the final concentration and another culture medium solution containing a substance to be examined at a concentration that is twice the final concentrations are each prepared, and then these solutions are mixed to each other at a ratio of 1:1.

The sol or solution may comprise a monomer such as acryl amide and culture medium components. This sol or solution is prepared by mixing the monomer, culture medium components, and, at need, a solvent. In this case, just before the start of the step (c), a polymerization initiator is added to the sol or solution.

The sol or solution may comprise fibrinogen and culture medium components. This sol or solution is prepared by mixing the fibrinogen, culture medium components, and, at need, a solvent. In this case, just before the start of the step (c), thrombin is added to the sol or solution. First, the fibrinogen is hydrolyzed to be fibrin monomer and then the fibrin monomer is polymerized.

Then, in step (c), the solution that has been poured into a concave part of a container is cooled by cooling the container, or monomers that are contained in the solution and that comes to a substance that composes a gelatinous material are bridged, i.e., polymerized. Thus, the solution is gelatinized. The cooling is conducted by air-cooling or intentionally.

The apparatus for culture thus prepared is used by pouring a culture medium solution into and placing cells or the like in a hollow that is made by taking out the article explained above. The making of the hollow, i.e., the taking out the article, may be conducted as step (d) that follows the step (c). Or, an user of the apparatus may make the hollow by taking out the article just before the user uses the apparatus.

If an apparatus for culture by which electric potentials of cultured cells can be measured is intended to be prepared, a container is used wherein on an inner bottom surface of the container electrodes (and leads) are pasted or printed. Or, before the step (a), step (x) of pasting or printing electrodes (and leads) on an inner bottom surface of the container is conducted. The electrodes may be formed on only a part of an inner bottom surface of a container where is to be covered by an article in step (a). The electrodes may be formed by a known method, e.g., those that are explained in Japanese Patent Early-publication Nos. Hei. 06-78889 and Hei. 06-296595, and Hei. 08-62209.

Further, after the step (c), step (e) may be conducted wherein a hole or a large hollow explained above is made in the layer of a gelatinous material. In other words, the step (e) comprises holing a part of a layer that has been made by gelatinizing a culture medium solution to make a hole or hollowing a part of the layer to make a large hollow. This step may be conducted by a user of the apparatus for culture, for example, just before the start of cell culture.

In the above, methods for preparing apparatuses for culture which accommodate the case where the material that is placed within a concave part of a container is a gelatinous material have been explained. Next, methods for preparing apparatuses for culture which can be used to make every apparatus for culture according to the first invention will be explained.

One example of the methods comprises step (A) of making within a concave part of a container a layer of at least one member (x) selected from the group consisting of a gelatinous material, a sponge material, and a mesh material, wherein the member (x) holds a solution that contains culture medium components, and step (B) of hollowing a part of the layer so that a part of an inner bottom surface of the container is bared to form at least one hollow.

The step (A) may specifically be conducted by one of the following methods (1) to (5):

(1) An aqueous sol solution (of which temperature is, e.g., about 40° C.) that turns to a gel by cooling and that contains medium components is poured into a concave part of a container and is cooled.

(2) An aqueous solution comprising culture medium components and a material that turns to a gel holding water by cross-linking (i.e., a monomer that turn to a gel holding water by polymerization) is poured into a concave part of a container and the material is cross-linked.

(3) An aqueous solution comprising culture medium components is impregnated into a sponge material or a mesh material.

(4) An aqueous sol solution (of which temperature is, e.g., about 40° C.) that turns to a gel by cooling is poured into a concave part of a container and is cooled, and after it is gelatinized, another aqueous solution comprising culture medium components is supplied to the gel to substitute for the solution held in the gel by diffusion.

(5) An aqueous solution comprising a material that turns to a gel holding water by cross-linking (i.e., a monomer that turn to a gel holding water by polymerization) is poured into a concave part of a container and the material is cross-linked, and after the gel is made, another aqueous solution comprising culture medium components is supplied to the gel to substitute for the solution held in the gel by diffusion.

The methods (4) and (5) are less practical because the another aqueous solution has to be exchanged some times to equilibrate the aqueous solution that is held by the gel.

The aqueous solution or the another aqueous solution may further comprises at least one substance to be examined. In the method (3), a substance to be examined may be previously adhered to the sponge material or the mesh material by lyophilization. In this case, merely by impregnating the aqueous solution comprising culture medium components into the sponge material or the mesh material just before its use, a layer of the material that holds an aqueous solution also comprising the substance to be examined may be prepared. The methods (3), (4), and (5) are usually applied to the case where the preciseness of the concentration of the substance to be examined in the member (x) is not required so much. If the substance to be examined should not be heated to a temperature of around 40° C., the method (3), (4), or (5) is selected because according to the method the substance to be examined is not heated.

In the step (B), a hollow or hollows are made by hollowing. A part or parts of a layer of, e.g., a gelatinous material is hollowed by using, e.g., a biopsy punch. When a container is used wherein on an inner bottom surface of the container electrodes (and leads) are pasted or printed, the hollow or hollows are made so that at least a part of the electrodes are bared. The step (B) may be conducted by a user of the apparatus for culture just before the start of cell culture. Or, just before the start of cell culture, a user may remove a pile or the like that has been previously made by cutting out a part of a layer of a gelatinous material with a biopsy punch.

Between the steps (A) and (B), or after the step (B), step (C) may be conducted wherein the hole or the large hollow that has been explained above is made.

Another example of the method for preparing the apparatus for culture according to the present invention comprises step (I) of making within a concave part of a container a layer of at least one member (x) selected from the group consisting of a gelatinous material, a sponge material, and a mesh material, step (II) of hollowing a part of the layer so that a part of an inner bottom surface of the container is bared to form at least one hollow, and step (III) of impregnating a solution that contains medium components into the layer.

The above step (I) may be conducted by one of the following methods (1) to (3):

(1) An aqueous sol solution (of which temperature is, e.g., about 40° C.) that turns to a gel by cooling is poured into a concave part of a container and is cooled, strictness.

(2) An aqueous solution comprising a material that turns to a gel holding water by cross-linking (i.e., a monomer that turn to a gel holding water by polymerization) is poured into a concave part of a container and the material is cross-linked.

(3) A sponge material or a mesh material is placed within a concave part of a container.

In the above method, the layer of the member (x) may further comprise at least one substance to be examined. Namely, in the step (I), a layer of at least one member (x) selected from the group consisting of a gelatinous material, a sponge material, and a mesh material wherein the layer holds at least one substance to be examined, may be made within a concave part of a container.

In this case, namely, if the layer holds at least one substance to be examined, the step (I) may be conducted by one of the following methods (1) to (3):

(1) An aqueous sol solution (of which temperature is, e.g., about 40° C.) that turns to a gel by cooling and that comprises a substance to be examined is poured into a concave part of a container and is cooled.

(2) An aqueous solution comprising a material that turns to a gel holding water by cross-linking (i.e., a monomer that turn to a gel holding water by polymerization) and a substance to be examined is poured into a concave part of a container and the material is cross-linked.

(3) A sponge material or a mesh material, to which a substance to be examined is adhered by, e.g., lyophilization, is placed within a concave part of a container. The method (3) is excellent in view of the storage stability of the substance to be examined.

Next, the step (II), i.e., a step of making a hollow by hollowing the layer, is conducted. Thereafter, in the step (III), a solution comprising culture medium components is supplied to the gelatinous material to substitute for the solution that is held in the gelatinous material by diffusion, or an aqueous solution comprising culture medium components is impregnated into the sponge material or the mesh material. If the layer of the member (x) comprises no substance to be examined, the solution comprising culture medium components that is used in the step (III) may further comprise at least one substance to be examined.

When the member (x) is a sponge material and/or a mesh material, the apparatus for culture of the first invention may also be prepared by the following method. Namely, the method comprises step (1) of making a hollow in a layered sponge or mesh material, step (2) of placing the layered sponge or mesh material in a concave part of a container, and step (3) of impregnating a solution that contains culture medium components into the layered sponge or mesh material.

In the step (1), a layered sponge or mesh material comprising at least one substance to be examined may be used. If the layered sponge or mesh material comprises no substance to be examined, the solution comprising culture medium components that is used in the step (3) may further comprise at least one substance to be examined.

Specific examples of the steps (1), (2), and (3) have been already explained in explanations for other methods for preparing the apparatus for culture of the first invention.

The culturing method of the sixth invention is characterized by comprising 1) preparing an apparatus for culture of the first invention, 2) putting a culture medium solution and cells or a piece of a tissue to be examined into a hollow or hollows of the apparatus, and 3) culturing the cells or the piece of the tissue by incubating the apparatus.

The solution that is held by the member (x) in the apparatus has principally the same composition as that of the solution that is poured into the hollow. Therefore, if the solution that is held by the member (x) also comprises a substance(s) to be examined, for pouring into the hollow a solution comprising a substance(s) to be examined should be used.

By using an apparatus in which the member (x) comprises no substance to be examined and another apparatus in which the member (x) comprises a substance(s) to be examined, the culturing method of the sixth invention may be conducted under same conditions. In this case, by comparing the courses of the cultures and their results, in morphology or biochemically or electrically, any change of cells or a tissue by the influence(s) of the substance(s) to be examined may be observed or studied.

The culturing method of the seventh invention is characterized by comprising 1) preparing an apparatus for culture of the first invention with the proviso that the solution containing culture medium components also comprises at least one substance to be examined and that the member (x) further has at least one member selected from the group consisting of a hole where the surface of the container in the concave part is not bared and a large hollow that has a volume larger than that of the hollow in the apparatus, 2) putting a culture medium solution comprising the substance to be examined and cells or a piece of a tissue to be examined into the at least one hollow of the apparatus, 3) putting the same solution into the hole and/or the large hollow of the apparatus, and 4) culturing the cells or the piece of the tissue by incubating the apparatus, while, at need, supplying the substance to be examined by exchanging the solution in the hole and/or the large hollow.

In the method of the seventh invention, an apparatus for culture of the present invention having a hollow and also a hole and/or a large hollow in its layer of the member (x) and comprising a culture medium solution that contains culture medium components and at least one substance to be examined, should be used.

In practicing the culturing methods of the present invention, it is preferable to avoid or prevent that the surface of the layer of the member (x) is dried up.

The culturing conditions such as an incubation temperature are properly selected depending on, e.g., a kind of a cell or tissue to be examined.

In the culturing methods of the present invention, various substances that are necessary for culture, e.g., culture medium components, and substances to be examined are supplied from the layer of the member (x). Because the culture medium solution in the hollow contacts with air, gases can be readily supplied or exchanged in the culturing methods of the present invention.

If the culture is intended to conduct over especially a long period of time, it is preferable to conduct a culturing method in which an apparatus of which the layer of the member (x) has a hole and/or a large hollow. In this method, a culture medium solution is poured into the hole and/or the large hollow. Therefore, the concentrations of the culture medium components of the solution in the hollow can be appropriately maintained over a long period of time. If it is necessary to culture for a longer period of time, it is good that the culture medium solution in the hole and/or the large hollow is exchanged or supplied at any time. The exchange or supply can be readily conducted without moving the cells or the like that have been studied or observed.

Further, if an apparatus is used in the culturing methods of the present invention in which a culture medium solution that is held by the member (x) also comprises a substance to be examined and the layer of the member (x) also has a hole and/or a large hollow, the concentration of the substance to be examined in a culture medium solution that exists in the hollow can be maintained for a long period of time. This is because the substance to be examined is supplied from the same culture medium solution in the hole and/or the large hollow.

The cultured cells or tissue can be studied or observed with lapse of time by an optical or electric determination as well as by using a magnified field of view by, e.g., a microscope, or an electrical image processing. If the optical or electric determination is used as an observational means, an apparatus having a structure such that a light ray passes through the hollow or such that electrodes are made on the surface of the container where corresponds to the bottom of the hollow should be used. Especially, it is clear that a cell culture for observation can be conducted with extremely high efficiency if an apparatus in which electrodes are made on the surface of the container where corresponds to the bottom of the hollow is used and the cells or the like are made to contact the electrodes.

If a culture medium solution flows during the determination of electric potentials, the electric potentials may fall into disorder. However, in the culturing method wherein an apparatus is used of which the layer of the member (x) has a hole or a large hollow an additional culture medium solution is supplied to the hole or the large hollow, in other words, the additional culture medium solution is not directly pored into a hollow where the electric potentials are determined. Thus, the flow of the culture medium solution scarcely occur in the hollow and, therefore, the electric potentials seldom falls into disorder.

If, to conduct the culturing method of the present invention, an apparatus is used of which the layer of the member (x) has plural hollows, same or different cells may be cultured at the same time by using the plural hollows. This culturing method is useful especially when it is intended to compare statuses of different cells under same cultural conditions.

According to the culturing methods of the present invention, the cell density against the amount of the culture medium solution can be locally increased, in other words, the volume of the culture medium solution can be increased as compared to the volume that is calculated based on the local cell density. This is because the area where the cells or the like are cultured is restricted by a gelatinous material or the like in a container.

If, to conduct the culturing method of the present invention, an apparatus is used in which the culture medium solution that is held by the member (x) also comprises a substance to be examined, the absolute amount of the substance to be examined can be increased. In this method, the substance to be examined is supplied to the culture medium solution in the hollow by the diffusion of the substance from the culture medium solution that is held by the member (x) to the culture medium solution in the area for culture, i.e., in the hollow, through the lateral of the area for culture.

The culturing methods of the present invention are advantageous as compared to conventional methods in the following points of view. Namely, the cells or the like are not diffused, i.e., are not moved, and influences of a medicine on cells or the like can be studied or observed with lapse of time over a long period of time.

According to the culturing methods of the present invention, the exchange or supply of the culture medium solution is unnecessary, or, the culture medium solution can be exchanged or supplied by using the hole and/or large hollow. Therefore, they can be prevented that, when, e.g., cells are cultured to cloning or a colony or colonies are assayed over a long period of time, a colony diffuses due to the exchange of the culture medium solution to be plural colonies and it becomes unclear whether the cells of the plural colonies are a clone or not.

In the culturing methods of the present invention, the bottom of the container is usually used to the study or observation of the cells or the like. While, medium components and/or a substance(s) to be examined are supplied through the lateral of the area for culture, i.e., the hollow. Namely, the supplies are conducted in lateral directions.

The culturing methods of the present invention are useful for not only suspension cells (non-adherent cells) but also when conditions of adherent cells or tissues are studied or observed with lapse of time. Especially when a piece of a tissue is cultured by using the apparatus of the first invention in which the layer of the member (x) has plural hollows, the position of each piece can be restricted and each piece can be studied or observed with lapse of time under same conditions including a concentration of a substance to be examined (e.g., a medicine). These are very advantageous.

The eighth invention relates to a method for studying or observing an influence of a substance to be examined on cells or a piece of a tissue comprising 1) preparing an apparatus for culture of the first invention with the proviso that the solution containing culture medium components comprises no substance to be examined, 2) putting the same solution and the cells or the piece of the tissue to be examined into the at least one hollow of the apparatus, 3) culturing the cells or the piece of the tissue by incubating the apparatus, 4) putting the substance to be examined into the at least one hollow during the culture, and 5) studying or observing the influence of the substance to be examined on the cells or the piece of the tissue.

In the eighth invention, first, cells or a piece of a tissue to be examined are cultured under such a condition that there is no substance to be examined. After they have been cultured for a certain period of time, a substance to be examined is added to the surroundings of the cells or the tissue, specifically, to the culture medium solution in the hollow, and then an acute influence of the substance to be examined is studied or observed. Specifically, immediately after the substance to be examined is added, changes in the morphology of the cells or tissue, changes in the cell potentials, change of the concentration of a specific substance that the cells or tissue release, or the like are studied or observed.

The ninth invention relates to a kit for making an apparatus for culture comprising a container having at least one concave part, culture medium components, a substance of which aqueous solution can be gelatinized, and (i) at least one article that can cover a part of a surface of the container in the concave part and has a certain height or (ii) a tool for hollowing a part of a layered gelatinous material which is made by gelatinizing an aqueous solution of the substance. By using the kit and according to a method for preparing an apparatus for culture of the present invention, the apparatus for culture of the first invention can be prepared.

A flat substrate for culture according to the present invention is one which can be used as a part of the apparatus for culture according to the first invention, with the proviso that the part is other than the container and that the member (x) in the apparatus for culture is a sponge material and/or a mesh material.

More specifically, one embodiment of the flat substrate for culture is one that is made of a sponge material and/or a mesh material, has at least one hollow, and holds culture medium components therein. Another embodiment of the flat substrate for culture is one that is made of a sponge material and/or a mesh material, has at least one hollow, and holds at least one substance to be examined. Further, another embodiment of the flat substrate for culture is one that is made of a sponge material and/or a mesh material, has at least one hollow, and holds medium components and at least one substance to be examined.

A flat substrate for culture refers to, e.g., one having a shape that is suitable for use by placing it in a laboratory dish, or one having a shape that is suitable for use by placing it in a well of a multi-well plate.

The substrate for culture may further have a hole and/or a large hollow explained above. The substrate for culture may hold a liquid such as water or a buffer.

The substrate for culture may be supplied, e.g., in a state that it is wrapped with a polymer sheet or film. It is used in a container such as a laboratory dish or a multi-well plate, at need.

According to the present invention, cells or a piece of a tissue can be concentrated in a hollow (i.e., a local place) that are surrounded by a gel or the like. As a result, while keeping the density of the cells or the tissue at a high level, the absolute number of the cells or the absolute amount of the tissue can be diminished and the ratio of a culture medium solution to the number of the cells or the amount of the tissue can be increased. Thus, it becomes possible to culture and to study or observe the cells or tissue for a long period of time.

According to the present invention, gases can be efficiently changed. Oxygen in air dissolves in a culture medium solution in a hollow (oxygen-supply in a vertical direction) and in a culture medium solution that is held by the member (x). Oxygen in the culture medium solution that is held by the member (x) moves and goes into the culture medium solution in the hollow (oxygen-supply in a horizontal direction). Thus, the culture medium solution in the hollow can contain a sufficient amount of air. While, gaseous carbon dioxide that is produced by cells and exists in the culture medium solution in the hollow moves and goes out in inverse direction to the air.

According to the present invention, up-regulating autocline or self product factors that cells produce to control environmental condition slowly diffuse from a culture medium solution in a hollow to a culture medium solution that is held by the member (x). In other words, the factors stay for a while in the culture medium solution in the hollow. This is advantageous to hasten cells' proliferation. Namely, the cells can enter a logarithmic growth phase earlier.

When, among apparatuses for culture according to the present invention, an apparatus for culture having a hole or a large hollow is used, a current of a culture medium solution scarcely occur in a hollow where cells exist. This is because the culture medium solution is exchanged or added through the hole or a large hollow. This is advantageous because the cells do not move even if the culture medium solution is exchanged or added.

Further, when, among apparatuses for culture according to the present invention, an apparatus for culture in which a medicine or the like has been contained in a culture medium solution is used, it becomes possible to study or observe the influences of the medicine or the like on the cells or the like for a long period of time. Especially when an apparatus for culture in which a medicine or the like has been previously held to a gel or the like is used, an advantage can also be obtained that everyone can readily culture cells or the like and can study or observe the influences of the medicine or the like on the cells or the like under an identical condition by merely preparing a culture medium solution and the cells or the like.

If an electrode has been pasted or printed on a surface of a bottom of a container, states of cells or the like can be readily studied, electrically. Namely, electric potentials of the cells can be measured.

According to the culturing method of the present invention, cells or a piece of a tissue are concentrated or restrictively located in a hollow (i.e., a local place) that is surrounded by a gel or the like. Therefore, it becomes possible to have the cells or the tissue growing in a good condition from the beginning of the culture and to study or observe them for a long period of time. If a medicine or the like has been held to a gel or the like, it becomes possible to study or observe the influences of the medicine or the like on the cells or the tissue for a long period of time. For example, even in the case where cells are cultured in a volume that corresponds to that of a well of a ninety-six-well culture plate (i.e., 200 µl), the cells can be readily cultured for a long period of time while studying or observing them. Thus, it is possible to study or observe the influences of the medicine or the like on the cells or the like for a long period of time.

In the culturing method of the present invention, cells or a piece of a tissue are concentrated in a local place. Therefore, this method is especially advantageous when the states of the cells or the tissue are optically or electrically studied.

EXAMPLES

Example 1

To 5 ml of distilled water, 0.05 g of agarose (Takara, L 03 "TaKaRa") was suspended (concentration: 1 w/v %). Then, to dissolve the agarose the suspension was heated at 121° C. for 15 minutes in an autoclave (Tomy Seiko, SS-320). A bottle containing the thus-obtained agarose solution was immersed in a water incubator set at 41° C. and the agarose solution was cooled to be 41° C.

While, a 0.3% trypan blue-containing 2×PBS solution (phosphate buffered saline, 2×PBS) was prepared. This solution was sterilized by making the solution pass through a nitrocellulose filter membrane having a pore size of 0.2 µm. A bottle containing the sterilized 0.3% trypan blue-containing 2×PBS solution was immersed in a water incubator set at 41° C. and the solution was heated to be 41° C.

At 41° C., the 1 w/v % agarose solution was mixed with the 0.3% trypan blue-containing 2×PBS solution in a volume ratio of 1:1 under an aseptic condition. The mixed solution (a PBS solution containing 0.5 w/v % agarose and 0.15% trypan blue) thus obtained was poured into wells of a twelve-well culture plate (Becton Dickinson and Company, FALCON MULTIWELL TISSUE CULTURE PLATE, Catalog No. 353043) in a volume of 2.3 ml per well. Theoretically, the depth of the liquid becomes about 6.1 mm. Also, this depth is nearly equal to that of the mixed solution in the case where the solution is poured into wells of a ninety-six-well culture plate in a volume of 0.2 ml per well.

After the mixed solution was poured into the wells, the culture plate was left cooling down for 30 minutes under room temperatures. Thus, the mixed solution was gelatinized. Hereafter, the gelatinized mixed solution will be designated as "a trypan blue-containing agarose gel."

In each well the layer of the trypan blue-containing agarose gel was punched out in its center by using a biopsy punch having a diameter of 6 mm and then a piece of the agarose gel was taken out while aspirating the gel with a Pasteur pipet. Thus, a hollow was formed.

Into each of thus-formed hollows 0.17 ml (theoretical depth: about 6.1 mm) of 1×PBS was poured. Then, the culture plate was left for five hours under conditions of a temperature of 37° C., humidity of 100%, and an atmosphere of 5% gaseous carbon dioxide and 95% air.

At appropriate time intervals, 0.02 ml of the PBS (it seemed that this contained trypan blue) in the hollow that had been made in the center of the gel layer in a well of the culture plate was taken out. The PBS thus taken out was diluted with 0.08 ml of pure water to reduce the concentrations of components by a factor of 5. The absorbance of the diluted PBS was determined at a wave length of 550 nm. The background was determined by using a diluted PBS (concentration: ⅕) containing no trypan blue. The value that was obtained by subtracting the absorbance of the background from that of the PBS that had been taken out from the PBS in the hollow and had diluted was specified as a true absorbance of the diluted PBS.

Before the start of the experiment, i.e., before the PBS is added to the hollow, the trypan blue-containing agarose gel was crushed and subjected to centrifugal separation at 14,000 rpm for 10 minutes (centrifuge: Tomy Seiko, MRX150, TMS-4). Also, after the PBS in the hollow was taken out (i.e., after the completion of the experiment), the trypan blue-containing agarose gel was crushed and subjected to centrifugal separation at 14,000 rpm for 10 minutes (centrifuge: Tomy Seiko, MRX150, TMS-4). From each of six samples (before the start of the experiment: three samples; after the completion of the experiment: three samples) supernatant (0.02 ml) was taken out and was diluted with 0.08 ml of pure water to reduce the concentrations of components by a factor of 5. The absorbance of the diluted supernatant was determined at a wave length of 550 nm. The value that was obtained by subtracting the absorbance of the background from that of the supernatant that had been extracted from the gel and had diluted was specified as a true absorbance of the diluted and gel-derived trypan blue-containing PBS (i.e., the diluted supernatant derived from the gel).

Figure 9:
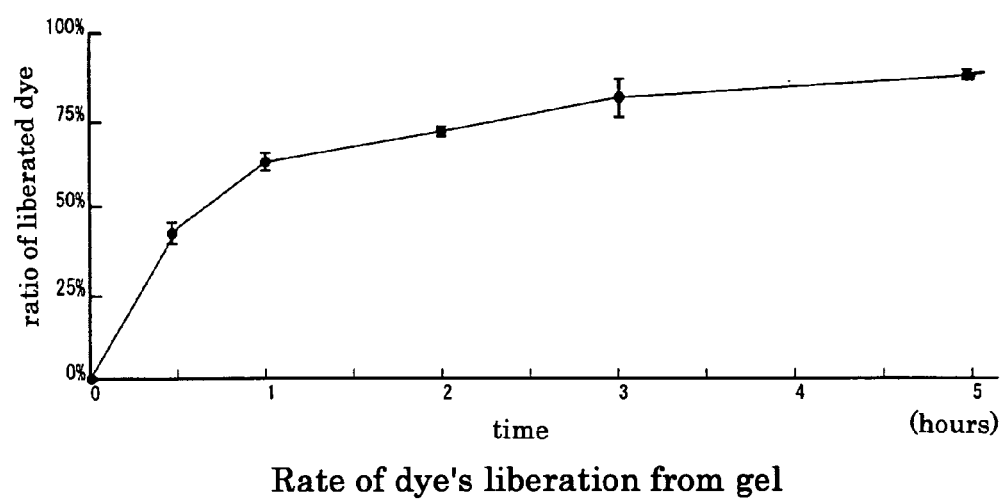
FIG. 9 is a graph in which a level of a diffusion or elution of trypan blue from a trypan blue-containing agarose gel to a culture medium solution in a hollow is shown.

The ratio of the true absorbance of the diluted PBS derived from the PBS in the hollow to that of the diluted and gel-derived trypan blue-containing PBS was calculated and expressed in percentage. FIG. 9 shows the result. Experiment was carried out in triplicate and the results were averaged. In FIG. 9 average values and error bars that indicate the ranges of standard deviations are shown.

From the result shown in FIG. 9, it can be understood that the trypan blue that had been held in the gel diffused and transferred to the PBS in the hollow of the gel. The concentration (expressed by the absorbance at a wave length of 550 nm) of the trypan blue in the diluted PBS derived from the PBS in the hollow became above 50% of the equilibrium value one hour after the incubation had started and above 80% of the equilibrium value three hours after the incubation had started.

The equilibrium value means the trypan-blue concentration when the trypan-blue concentration of the diluted PBS that is derived from the PBS in the hollow is the same as that of the diluted and gel-derived trypan blue-containing PBS that is derived from the PBS held in the gel. The total volume of the PBS in the hollows of the gel is extremely lower than the volume of the PBS in the gel. Therefore, the concentration of the trypan blue in the diluted and gel-derived trypan blue-containing PBS (i.e., in the diluted supernatant derived from the gel) is nearly the same as the equilibrium value.

As stated above, it was confirmed that the trypan blue that had been held in the gel diffused and transferred in a short time of period to the PBS in the hollow that had been made by hollowing the gel.

Example 2

Agarose (Takara, L 03 "TaKaRa") was added to ultrapure water in a ratio of 1 gram per 100 ml of the water and was suspended (concentration: 1 w/v %). Then, to dissolve the agarose the suspension was heated at 121° C. for 15 minutes in an autoclave (Tomy Seiko, SS-320). A bottle containing the thus-obtained agarose solution was immersed in a water incubator set at 41° C. and the agarose solution was cooled to be 41° C.

While, a powdery GIBCO™ Medium RPMI 1640 (IN-VITROGEN CORPORATION, Cat. No. 31800-014) (glutamine was contained) was added to ultrapure water in a ratio of 10.4 gram per 500 ml of the water and was dissolved (concentration: about twice the final concentration). This solution was sterilized by making the solution pass through a nitrocellulose filter membrane having a pore size of 0.2 µm. Thus, 2×RPMI 1640 medium solution was prepared.

To 30 ml of this medium solution, 2-mercaptoethanol, penicillin, and streptomycin were added under an aseptic condition in such amounts as to be concentrations of 100 µM, 50 U/ml, and 50 ng/ml, respectively. Then, to the thus-obtained solution, 6 ml of heat-inactivated bovine fetal serum was added. To the thus-obtained heat-inactivated bovine fetal serum/2×RPMI 1640 medium solution, interleukin 2 (IL-2, mouse, recombinant, SIGMA I-0523) was added in a ratio of 5 ng per ml of the solution. A bottle containing the thus-prepared heat-inactivated bovine fetal serum/2×RPMI 1640 medium solution was immersed in a water incubator set at 41° C. and the solution was heated to be 41° C.

At 41° C., the 1 w/v % agarose solution was mixed with the heat-inactivated bovine fetal serum/2×RPMI 1640 medium solution in a volume ratio of 1:1 under an aseptic condition. The mixed solution thus obtained was poured into wells of a twelve-well culture plate (Becton Dickinson and Company, FALCON MULTIWELL TISSUE CULTURE PLATE, Catalog No. 353043) in a volume of 2.5 ml per well.

After the mixed solution was poured into the wells, the culture plate was left cooling down for 30 minutes or more under room temperatures. Thus, the mixed solution was gelatinized. Hereafter, the gelatinized mixed solution will be designated as "an IL-2-containing agarose gel."

In each well the layer of the IL-2-containing agarose gel was punched out in its center by using a biopsy punch having a diameter of 6 mm to form a hollow.

Into each of the thus-formed hollows, 0.15 ml of a solution was poured, which solution had been made by mixing an heat-inactivated bovine fetal serum/2×RPMI 1640 medium solution not containing IL-2 with ultrapure water in a volume ratio of 1:1. Then, the culture plate was left under conditions of a temperature of 37° C., humidity of 100%, and an atmosphere of 5% gaseous carbon dioxide and 95% air. The volume ratio of the gel to the hollow is 3.80:0.322. Thus, when the IL-2 concentration reaches to equilibrium between solutions contained in the gel and in the hollow, the concentration should be about 4.6 ng/ml.

At appropriate time intervals after the solution was poured into the hollows, from three hollows solutions were taken out in an amount of 0.02 ml per hollow. The three solutions that were taken out at the same time were gathered, poured into a tube having a volume of 0.2 ml, and refrigerated at −20° C. After sampling and refrigeration of the solutions were completed, all refrigerated samples were thawed. Then, by using mouse IL-2 Elisa Ready-SET-Go! (e-Bioscience, Cat. No. 88-70224-77), IL-2 concentrations of the samples were determined according to the protocol stated in the instruction.

Figure 10:
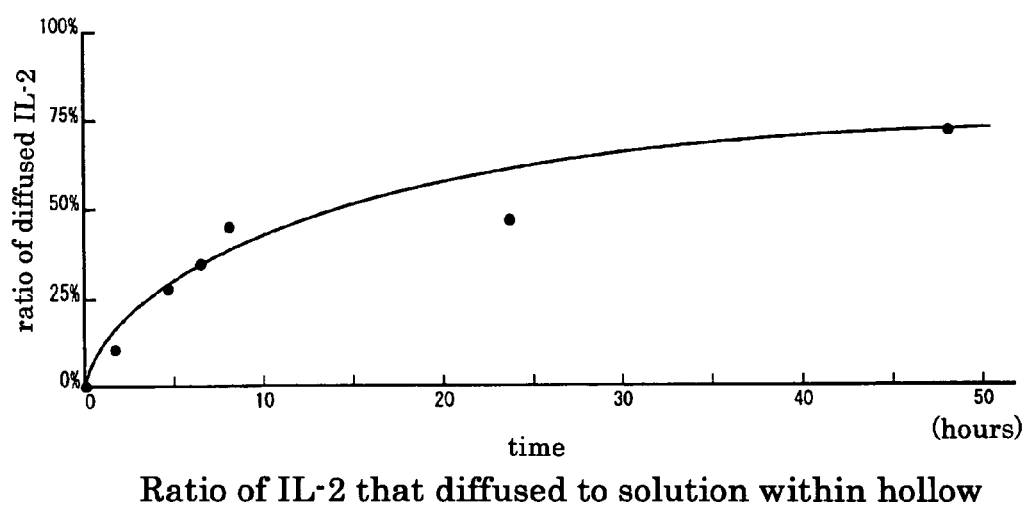
FIG. 10 is a graph in which a level of a diffusion or elution of IL-2 from an IL-2-containing agarose gel to a culture medium solution in a hollow is shown.

FIG. 10 shows the result. The numerical values of the vertical axis were calculated as follows: After the solutions in the hollows were taken out, the IL-2-containing agarose gel was crushed and a solution was squeezed of the gel. For this solution an IL-2 concentration was determined in the same way as explained above. The ratios of the IL-2 concentrations of the solutions that had been taken out from the hollows to the IL-2 concentration of the solution that had been squeezed out from the gel were calculated and expressed in percentage.

From the result shown in FIG. 10, it can be understood that IL-2 that had been held in the gel diffused and transferred to the solution in the hollow of the gel. The IL-2 concentration of the solution contained in the hollow became about 10% of the equilibrium value two hours after the incubation had started, at least 30% of the equilibrium value within six hours, and about 70% forty-eight hours after the incubation had started.

From the above result, it was confirmed that IL-2 that was held in the gel diffused and transferred to the solution in the hollow at a relatively slow rate.

Example 3

In a medium bottle, 0.2 g of Agarose (Takara, L 03 "TaKaRa") was suspended in 20 ml of ultrapure water (concentration: 1 w/v %). Then, to dissolve the agarose the suspension was heated at 121° C. for 15 minutes in an autoclave (Tomy Seiko, SS-320). A bottle containing the thus-obtained agarose solution was immersed in a water incubator set at 41° C. and the agarose solution was cooled to be 41° C.

While, 10.4 g of a powdery GIBCO™ Medium RPMI 1640 (INVITROGEN CORPORATION, Cat. No. 31800-014) was dissolved in 500 ml of ultrapure water (concentration: about twice the final concentration). This solution was sterilized by making the solution pass through a nitrocellulose filter membrane having a pore size of 0.2 μm. Thus, 2×RPMI 1640 medium solution was prepared.

To 100 ml of the 2×RPMI 1640 medium solution, 100 ml of heat-inactivated bovine fetal serum was added under a aseptic condition. The thus-obtained heat-inactivated bovine fetal serum/2×RPMI 1640 medium solution was poured into four sterile bottles in an amount of 30 ml per bottle. The sterile bottles were immersed in a water incubator set at 41° C. and the medium solutions therein were heated to be 41° C.

To medium solutions in three sterile bottles among the above four sterile bottles, aminopterin (Sigma, Hybri-Max, Code No. A5159, a folic acid antagonist) (concentration: fifty times the aminopterin concentration in a HAT medium in the case where a HAT selective culture is conducted to prepare a monoclonal-antibody productive hybridoma) was added in an amount such that its volume is one-twenty fifth (1/25) of the total volume of the medium solution and aminopterin (i.e., 1.2 ml of 50×aminopterin). The concentration of aminopterin became twice that in the HAT medium.

To a medium solution containing aminopterin in one sterile bottle, HT supplements (GIBCO/Invitrogen, Code No. 11067-030, a mixture of hypoxanthine and thymidine) (concentrations: one hundred times the concentrations of hypoxanthine and thymidine in the HAT medium) were added in amounts such that their total volume is one-fiftieth (1/50) of the total volume of the medium solution containing aminopterin and the HT supplements (i.e., 0.6 ml of 100× HT). The concentrations of hypoxanthine and thymidine became twice those in the HAT medium.

To a medium solution containing aminopterin in another sterile bottle, the HT supplements were added in amounts such that their total volume is one-five hundredth (1/500) of the total volume of the medium solution containing aminopterin and the HT supplements. The concentrations of hypoxanthine and thymidine became one-fifth of those in a HAT medium. The sterile bottles were continuously heated at 41° C.

As explained above, medium solution No. 1 contained no aminopterin nor HT supplements [hereafter "A(−), H(−)"], medium solution No. 2 contained aminopterin and no HT supplements [hereafter "A(+), H(−)"], medium solution No. 3 contained aminopterin and HT supplements [hereafter "A(+), H(+)"], and medium solution No. 4 contained aminopterin and HT supplements with the proviso that the concentrations of hypoxanthine and thymidine were one-tenth of those of medium solution No. 3 [hereafter "A(+), H(0.1+)"].

Then, at 41° C., 20 ml of the 1 w/v % agarose solution was mixed with 20 ml of medium solution No. 3 under an aseptic condition. By this, concentrations of the culture medium components of RPMI 1640 medium, heat-inactivated bovine fetal serum, aminopterin, and HT supplements, each of which had been prepared in an concentration of twice the final concentration, became one half of their concentrations in medium solution No. 3. The concentrations of hypoxanthine, aminopterin, and thymidine are equal to those, respectively, in a HAT medium in the case where a HAT selective culture is conducted to prepare a monoclonal-antibody productive hybridoma.

The mixed solution thus obtained was poured into wells (diameter: 22 mm) of a twelve-well culture plate (Becton Dickinson and Company, FALCON MULTIWELL TISSUE CULTURE PLATE, Catalog No. 353043) in a volume of 2.3 ml per well.

While, 10 ml of ultrapure water which had been sterilized by filtration was added to 10 ml of medium solution No. 3. Thus, a culture medium solution having the same composition as that of the mixed solution that had been poured into wells of the twelve-well culture plate, except that it did not contain agarose, was prepared. This solution was used as a control solution.

After the mixed solution was poured into the wells, the culture plate was left cooling down for 60 minutes or more under room temperatures. Thus, the mixed solution was gelatinized. Hereafter, the gelatinized mixed solution will be designated as "an aminoprerin/HT-containing agarose gel."

In each well the layer of the aminoprerin/HT-containing agarose gel was punched out in its center by using a biopsy punch having a diameter of 6 mm to form a hollow.

Into each of the thus-formed hollows, 0.17 ml of the culture medium solution not containing agarose (i.e., the control solution) was poured. Then, the culture plate was left in an incubator under conditions of a temperature of 37° C., humidity of 100%, and an atmosphere of 5% gaseous carbon dioxide and 95% air.

The culture plate was taken out from the incubator. Then, the culture medium solutions in the hollows were removed by aspiration. While, a hybridoma suspension was prepared. This suspension contained the culture medium solution and KNA14.2 (a hybridoma which produces a mouse monoclonal antibody against human Aggrecan peptide position 342–350) in an amount of $1\times10^6$ per ml of the solution. Into the hollows, the hybridoma suspension were poured in an amount of 0.1 ml per well. Then, the culture medium solutions was added in an amount of 0.05 ml per well. The culture plate was incubated under conditions of a temperature of 37° C., humidity of 100%, and an atmosphere of 5% gaseous carbon dioxide and 95% air.

As a control for comparison, a ninety-six-well culture plate (Nalge Nunc International, Nunc 96-well plate, Catalog No. 167008) was used. Into wells of the culture plate having a diameter of 6.4 mm, the hybridoma suspension and the culture medium solution were poured in amounts of 0.1 ml per well and 0.1 ml per well, respectively. Thus, the total volume of a liquid in a well was 0.2 ml. This 96-well plate was incubated under the same conditions.

A calculated depth of a liquid in the case where 0.2 ml of the liquid is poured into a well of the ninety-six-well culture plate is almost equal to that of a liquid in the case where 2.3 ml of the liquid is poured into a well of the twelve-well culture plate. Namely, influence of the difference between their depths is theoretically minimized.

Two, three, and four days after the culture was started, from each of the well of the ninety-six-well culture plate and the hollow that had been formed in a gel in a well of the twelve-well culture plate (hereafter, they may be written as "the well and the hollow" for our accommodation), 10 μl of culture supernatant (1) was sampled. Then, to substitute for culture supernatant (1), 10 μl of TritonX-100/PBS was poured into the well and the hollow. The ninety-six-well culture plate and the twelve-well culture plate were left under room temperatures for thirty minutes. By this, living cells died and a liquid containing LDH (lactose dehydrogenase) that had been held in the cells became to diffuse into culture supernatant.

Thirty minutes after the TritonX-100/PBS was poured, from each of the well and the hollow 10 μl of culture supernatant (hereafter "culture supernatant (2)") was cautiously taken out. Culture supernatants (1) and (2) were diluted with PBS in a ratio of 1:9 (culture supernatant: PBS). To each of diluted supernatants (1) and (2), MTX-LDH Reagent (Kyokuto Pharmaceutical Industrial Co., Ltd.) was added. A color reaction was caused by LDH that had diffused into the culture supernatants. Then, the absorbance was determined at a wave length of 550 nm.

Because the gel is readily crushed, in this experiment the gel cannot be previously centrifuged to wash it. Therefore, if only culture supernatant (2) is used to determine the amount of LDH, LDH that is derived from cells that had already died during the culture (hereafter "died cells") is also determined. To exclude the LDH that is derived from died cells, the LDH value (after dilution with PBS) of culture supernatant (1) that had been taken out before 1% Triton X-100 was added was subtracted from the LDH value (after dilution with PBS) of culture supernatant (2) that was taken out after 1% Triton X-100 had been added.

Figure 11:
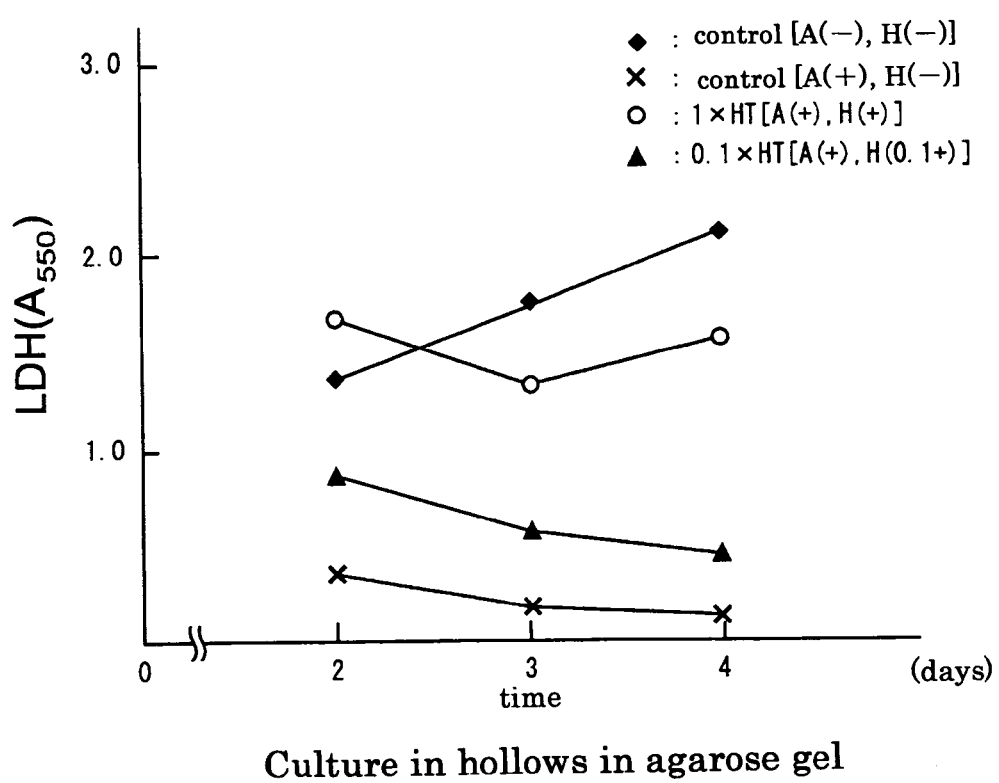
FIG. 11 is a graph showing a result of an experiment (inhibition against cell proliferation by aminopterin and its compensation by hypoxantin) according to the method of the present invention in which cells were cultured in hollows that were formed in agarose gels.

Three samples were determined for each culture supernatant. In FIG. 11 (Inventive Examples in which gel and a twelve-well culture plate were used) and FIG. 12 (Examples as controls, a ninety-six-well culture plate was used), the average values are shown.

Figure 12:
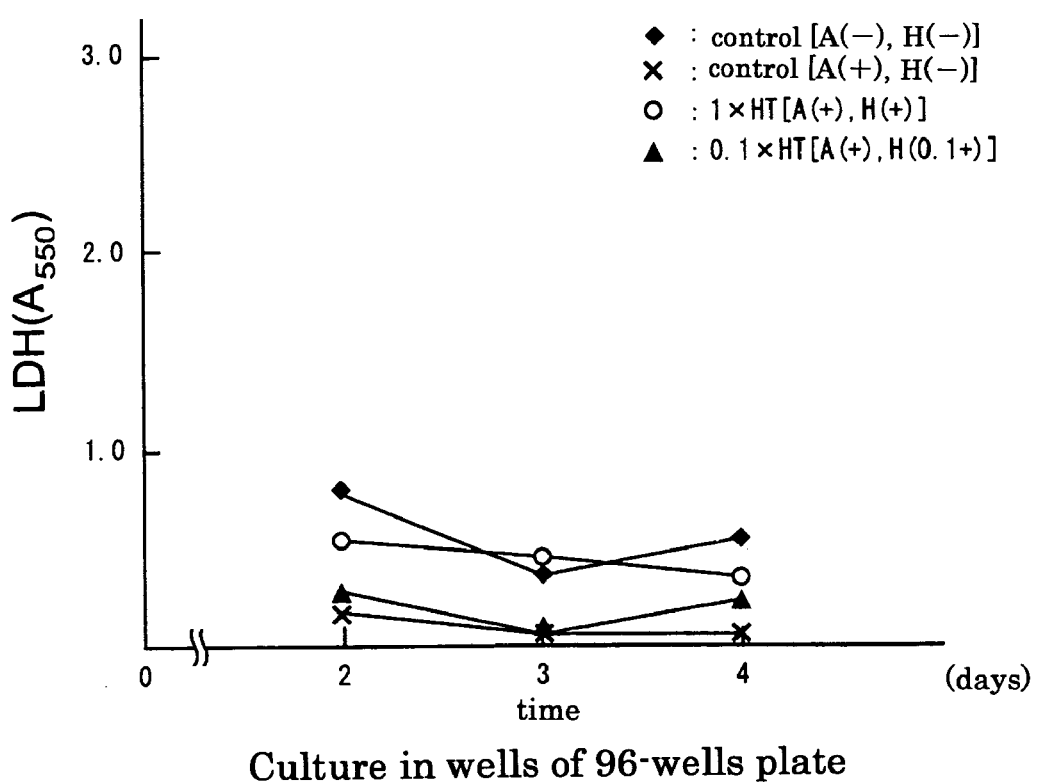
FIG. 12 is a graph showing a result of an experiment (inhibition against cell proliferation by aminopterin and its compensation by hypoxantin) according to a conventional method in which cells were cultured in wells of a ninety-six-well culture plate.

The above experiment was repeated except that medium solution No. 1 ([A(−), H(−)]), medium solution No. 2 ([A(+), H(−)]), or medium solution No. 4 ([A(+), H(0.1+)]) was used instead of medium solution No. 3 ([A(+), H(+)]). FIGS. 11 and 12 also show the results of these experiments.

From FIGS. 11 and 12, it can be understood that the amount of LDH produced in the culture in the hollows that were formed in gels is more than that of LDH produced in the culture in the wells (volume: 200 μl) of the ninety-six-well culture plate. Namely, the cells cultured in the hollows that were formed in gels were more active. Therefore, in the case where the cells were cultured in the hollows that were formed in gels, it is more clearly shown that inhibition against cell proliferation by aminopterin ([A(+), H(−)]) was compensated with hypoxantin ([A(+), H(0.1+)] and [A(+), H(+)]) through the salvage pathway.

Example 4

The experiment in Example 3 was repeated except that a hybridoma suspension containing hybridoma KNA14.2 in an amount of $1\times10^5$ per ml was used instead of the hybridoma suspension containing that hybridoma in an amount of $1\times10^6$ per ml, for culturing the hybridoma for a longer period of time.

Four and six days after the culture was started, from each of the well and the hollow, 10 μl of culture supernatant (1) was sampled. Then, to substitute for culture supernatant (1), 10 μl of Triton X-100/PBS was poured into the well and the hollow. The ninety-six-well culture plate and the twelve-well culture plate were left under room temperatures for thirty minutes. Thirty minutes after the Triton X-100/PBS was poured, from each of the well and the hollow 10 μl of culture supernatant (2) was cautiously taken out. Culture supernatants (1) and (2) were diluted with PBS in a ratio of 1:9 (culture supernatant: PBS). To each of diluted supernatants (1) and (2), MTX-LDH Reagent (Kyokuto Pharmaceutical Industrial Co., Ltd.) was added. By the same way as that in Example 3 the amount of LDH was determined.

Figure 13:
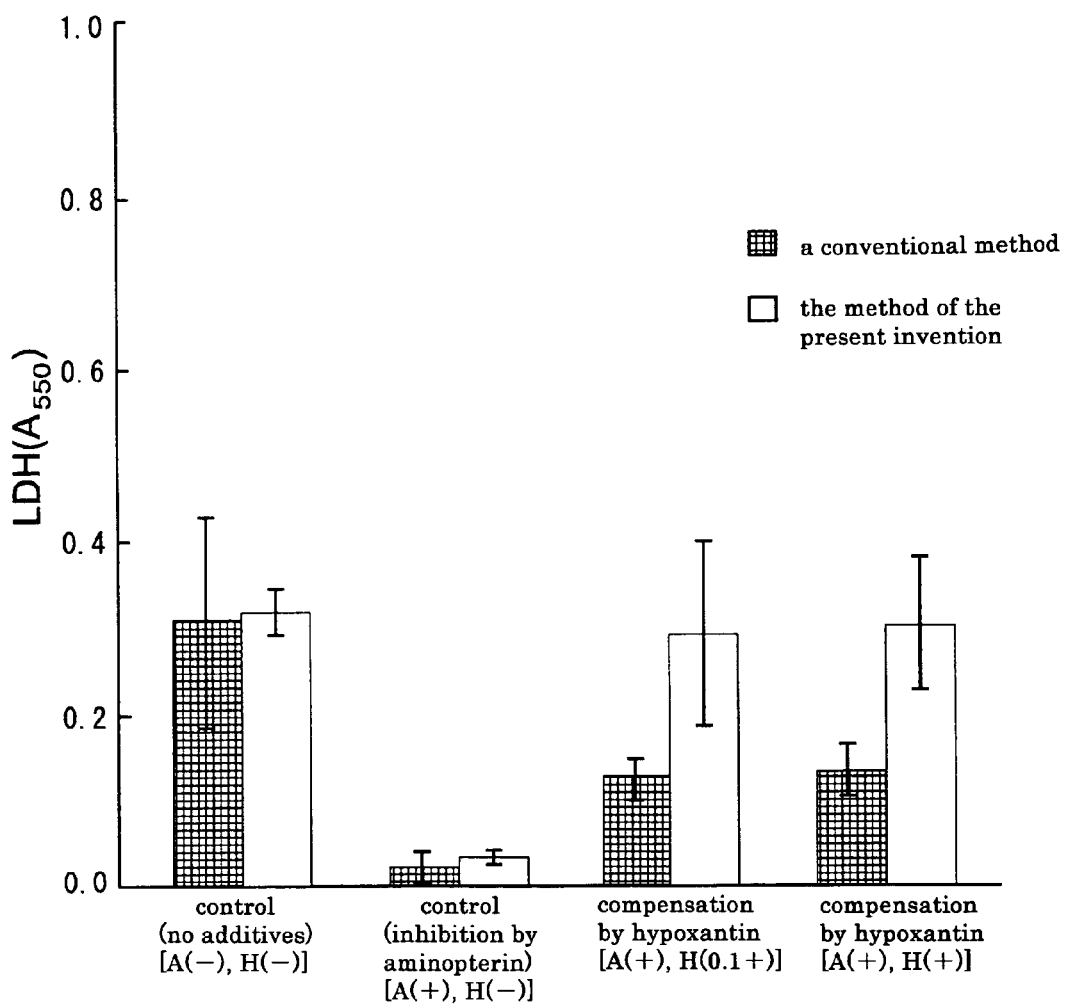
FIG. 13 is a graph showing results of experiments (inhibition against cell proliferation by aminopterin and its compensation by hypoxantin) in which cells were cultured in wells of a ninety-six-well culture plate (a conventional method) or in hollows that were formed in agarose gels (the method of the present invention).
Figure 14:
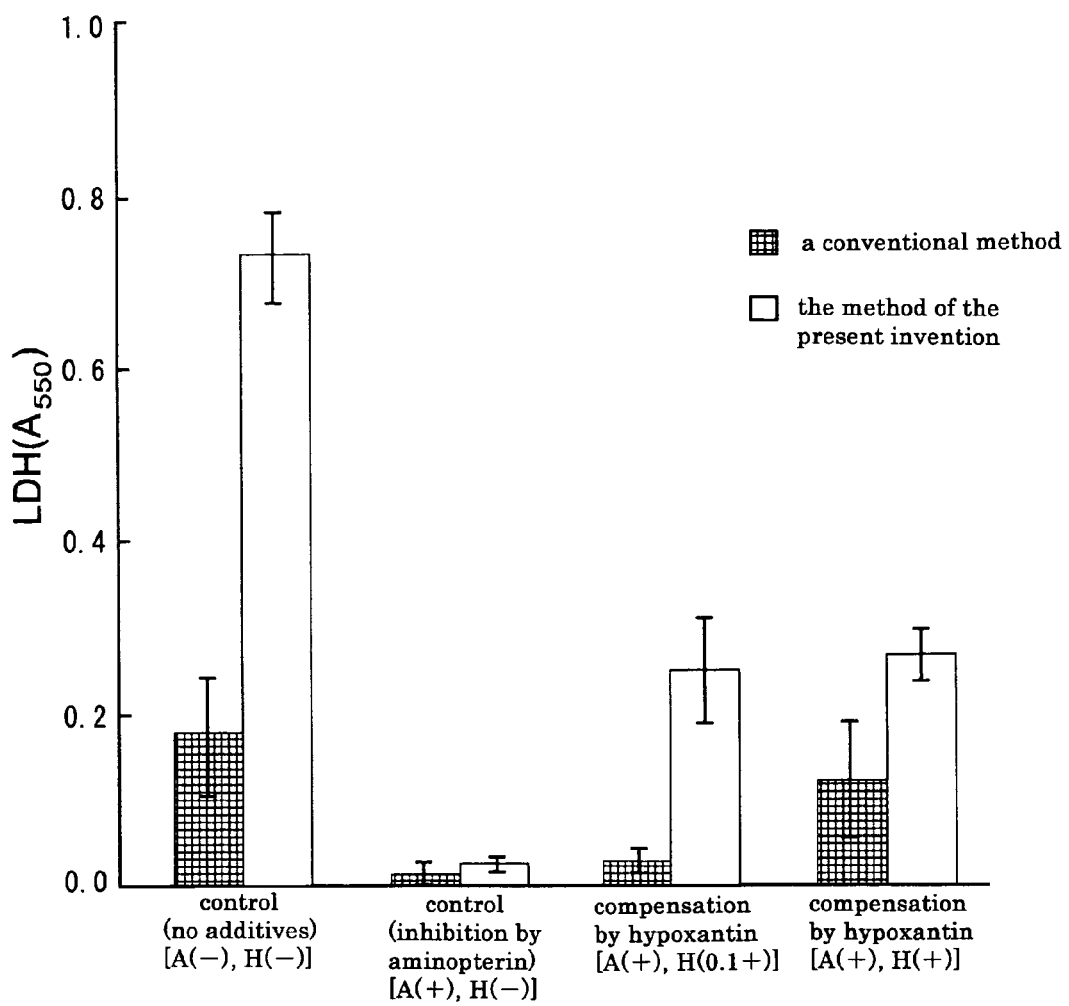
FIG. 14 is a graph showing results of experiments (inhibition against cell proliferation by aminopterin and its compensation by hypoxantin) in which cells were cultured in wells of a ninety-six-well culture plate (a conventional method) or in hollows that were formed in agarose gels (the method of the present invention).

Three samples were determined for each culture supernatant. In FIG. 13 (measurements after four days' culture)

and FIG. 14 (measurements after six days' culture), the average values and standard deviations are shown.

From FIG. 13, it can be understood that in the conventional method (culture by using a ninety-six-well culture plate) inhibition against cell proliferation by aminopterin ([A(+), H(−)]) could be compensated with hypoxantin ([A(+), H(0.1+)] and [A(+), H(+)]) only in a level of about 40%. On the other hand, in the method of the present invention (culture in a hollow that was formed in a gel) the inhibition could be compensated in a level of about 100%, because the cells were more active.

Further, from FIG. 14 it can be understood that in the conventional method inhibition against cell proliferation by aminopterin could be scarecely compensated with hypoxantin when the culture was conducted under a condition that the concentration of hypoxantin is low ([A(+), H(0.1+)]). This is because the hypoxantin was depleted with the lapse of time. On the other hand, in the method of the present invention, even if the culture was conducted under a condition that the concentration of hypoxantin is low ([A(+), H(0.1+)]) the inhibition could be compensated with hypoxantin in the same level as that in the culture using the hypoxantin in its usual concentration ([A(+), H(+)]) and in a higher level than that of the conventional method. This is because in the method of the present invention the hypoxantin was continuously supplied through the gel.

Example 5

The cell culture in Example 3 was repeated except that a hybridoma suspension containing hybridoma KNA14.2 in an amount of $5 \times 10^5$ per ml was used instead of the hybridoma suspension containing that hybridoma in an amount of $1 \times 10^6$ per ml.

Three days after the culture was started, states of cells that were cultured in a RPMI1640 medium solution containing aminopterin and serum ([A(+), H(−)]) and that were cultured in a RPMI1640 medium solution containing aminopterin, HT supplements, and serum ([A(+), H(+)]) were photographed under a microscope (magnification: ×200).

Figure 15:
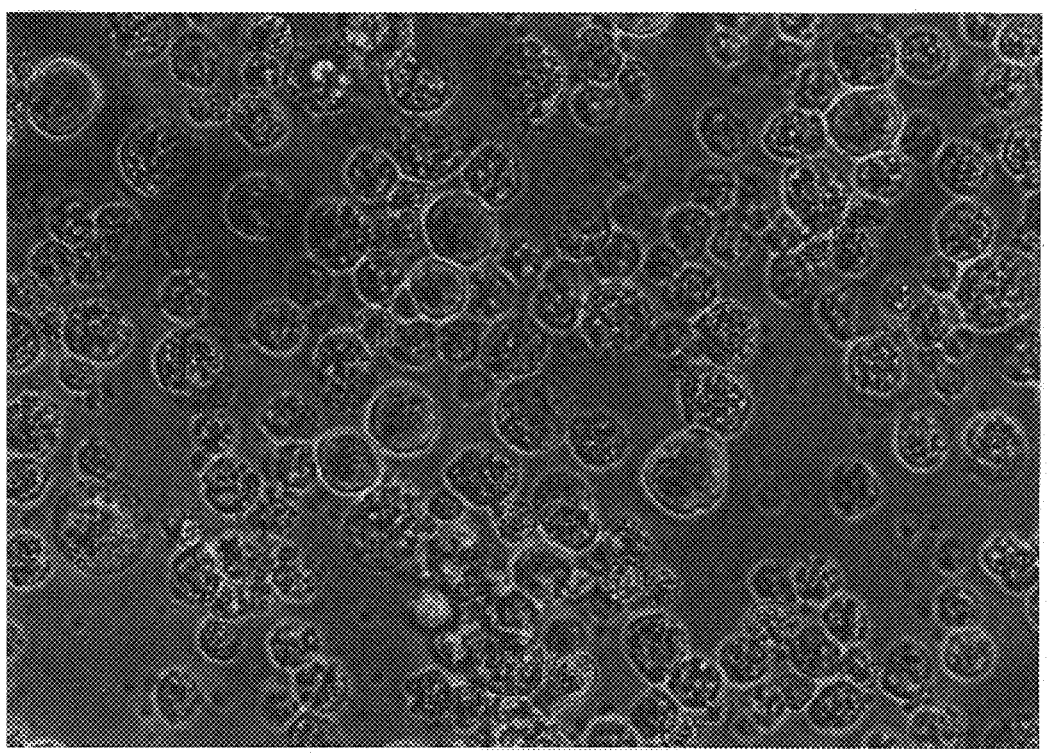
FIG. 15 is a photomicrograph (magnification: ×200) of cells that were cultured according to a conventional method.
Figure 16:
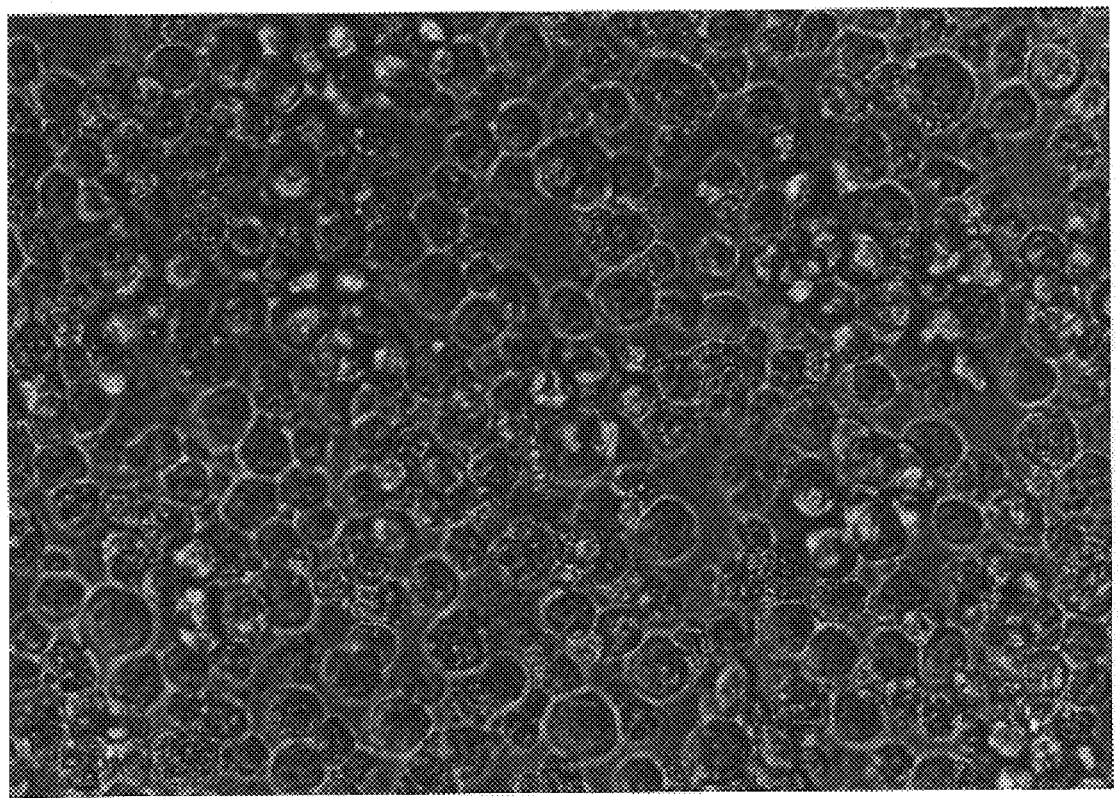
FIG. 16 is a photomicrograph (magnification: ×200) of cells that were cultured according to a conventional method.
Figure 17:
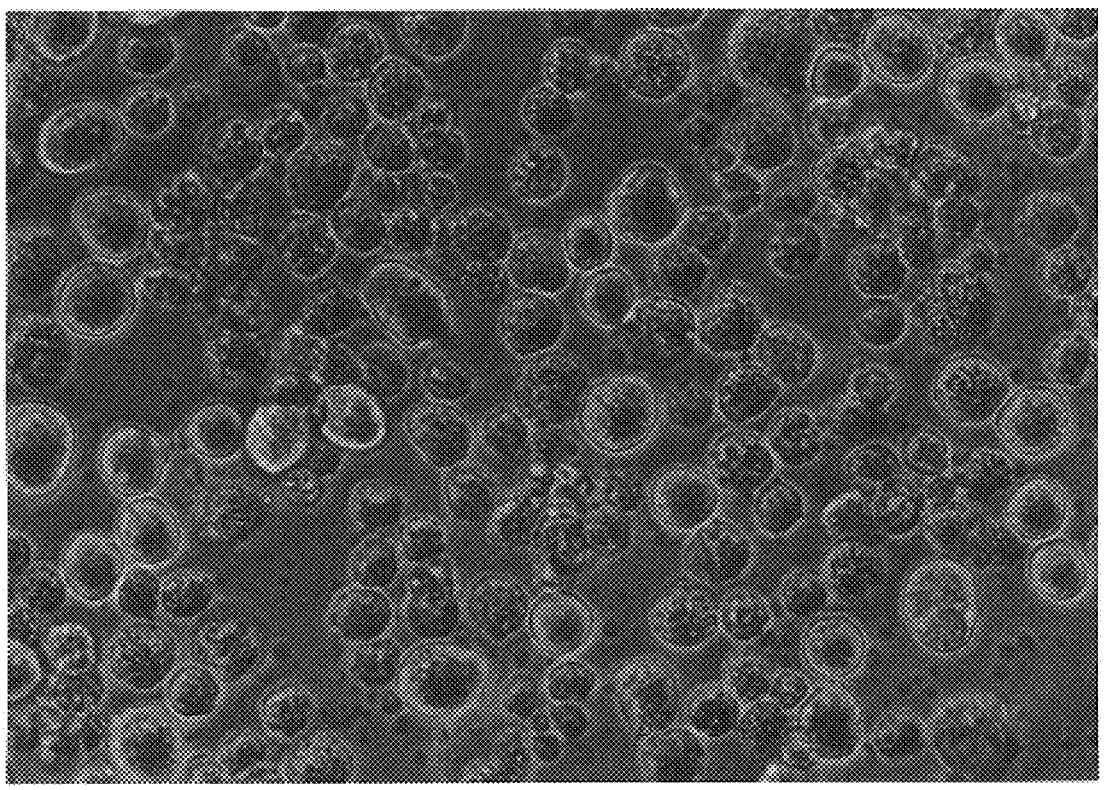
FIG. 17 is a photomicrograph (magnification: ×200) of cells that were cultured according to the method of the present invention.
Figure 18:
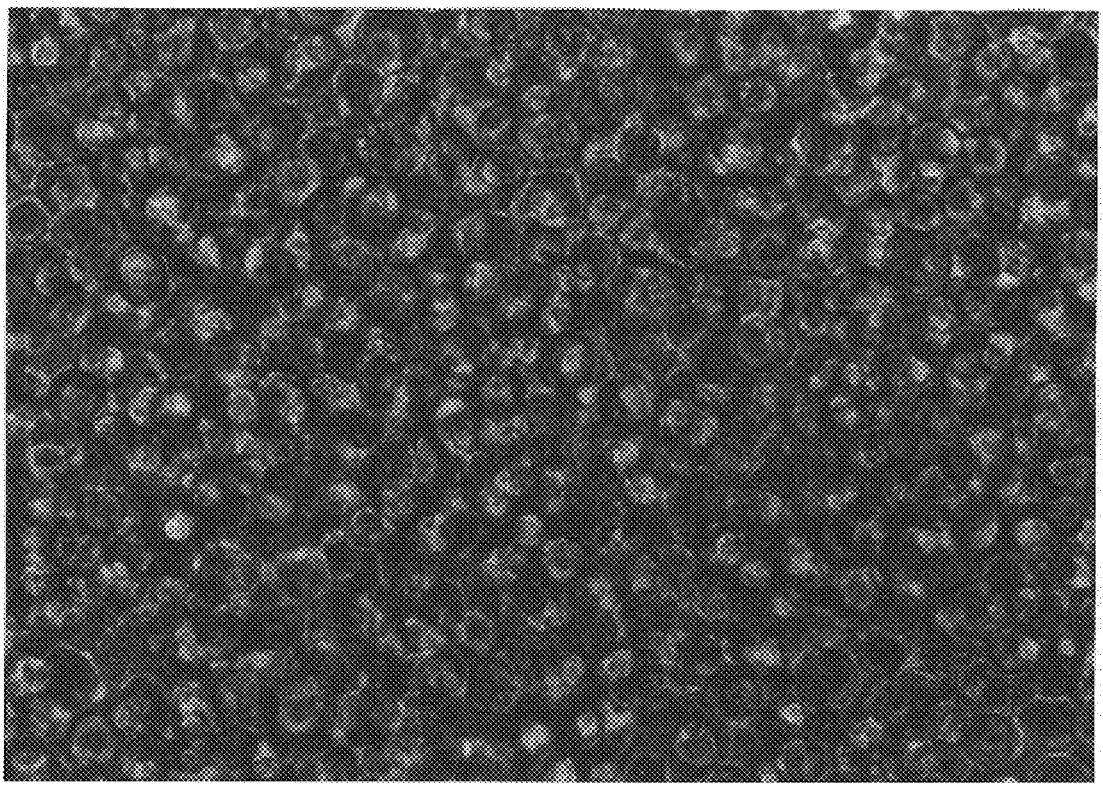
FIG. 18 is a photomicrograph (magnification: ×200) of cells that were cultured according to the method of the present invention.

FIGS. 15 and 16 show cells that were cultured in the RPMI1640 medium solution containing aminopterin and serum ([A(+), H(−)]) and cells that were cultured in the RPMI1640 medium solution containing aminopterin, HT supplements, and serum ([A(+), H(+)]), respectively, by the conventional method (culture by using a ninety-six-well culture plate). FIGS. 17 and 18 show cells that were cultured in the RPMI1640 medium solution containing aminopterin and serum ([A(+), H(−)]) and cells that were cultured in the RPMI1640 medium solution containing aminopterin, HT supplements, and serum ([A(+), H(+)]), respectively, by the method of the present invention (culture in a hollow that was formed in a gel).

As is clear by comparing FIG. 16 with FIG. 18, in the case where the cells were cultured by the method of the present invention (see FIG. 18), the number of the cells were large (i.e., the cells were dense) and their states were well. Namely, inhibition against cell proliferation by aminopterin had been compensated with hypoxantin. Also in comparison of FIG. 15 (conventional method) with FIG. 17 (method of present invention), both of which show the level of the inhibition against cell proliferation by aminopterin, it can be understood that in the case where the cells were cultured by the method of the present invention (see FIG. 17), the number of the cells were large (in other words, there were only a small number of voids, i.e., places where there were no cells) and their states were well.

In the specification and drawings, the present invention has been specifically explained with reference to preferable embodiments. Those skilled in the art will appreciate that numerous modifications may be made without departing from the spirit of the present invention. Thus, it should not be recognized that the present invention is limited to those embodiments and the scope of the present invention is to be determined only by the following claims.

What we claim is:

1. An apparatus for culture, comprising a container having at least one concave part and at least one member (x) selected from the group consisting of a gelatinous material, a sponge material, and a mesh material, wherein the member (x) is placed within the concave part of the container, has at least one hollow by which a part or parts of a surface of the container in the concave part is bared, and holds a solution containing culture medium components, and wherein on the bared part of the surface of the container, an electrode is pasted or printed.

2. An apparatus for culture, comprising a container having at least one concave part and at least one member (x) selected from the group consisting of a gelatinous material, a sponge material, and a mesh material, wherein the member (x) is placed within the concave part of the container, has at least one hollow by which a part or parts of a surface of the container in the concave part is bared, holds a solution containing culture medium components, and further has at least one member selected from the group consisting of a hole where the surface of the container in the concave part is not bared and a large hollow that has a volume larger than that of the hollow.

3. A process for preparing an apparatus for culture comprising:
    step (a) of placing within a concave part of a container an article that can cover a part of a surface of the concave part, has a certain height, and is configured to make a hollow in a layer of gelatinous material that is made by step (c), wherein the hollow is configured to hold a solution in use;
    step (b) of pouring into the concave part a solution that contains culture medium components and at least one substance to be examined, and that can be gelatinized;
    step (c) of gelatinizing the solution; and
    step (d) of removing the article to expose the hollow in the layer of the gelatinous material.

4. A process for preparing an apparatus for culture, comprising:
    step (a) of placing within a concave part of a container an article that can cover a part of a surface of the concave part and has a certain height;
    step (b) of pouring into the concave part a solution that contains culture medium components and that can be gelatinized; and
    step (c) of gelatinizing the solution,
    wherein the container has an electrode that has been pasted or printed on the surface of the concave part and in step (a) the article is placed so that it covers at least a part of the electrode.

5. A process for preparing an apparatus for culture, comprising:
    step (a) of placing within a concave part of a container an article that can cover a part of a surface of the concave part and has a certain height;
    step (b) of pouring into the concave part a solution that contains culture medium components and that can be gelatinized;
    step (c) of gelatinizing the solution; and step (e) of (i) holing a part of a layer that has been made by gelatinizing the solution to form a hole where a surface of the concave part is not bared, or (ii) hollowing a part of a layer that has been made by gelatinizing the solution to form a large hollow which has a volume larger than that of a hollow which is made by removing the article and by which a part of a surface of the concave part is bared, wherein the step (e) is conducted after the step (c).

6. A process for preparing an apparatus for culture, comprising:

step (A) of making, within a concave part of a container, a layer of at least one member (x) selected from the group consisting of a sponge material and a mesh material, wherein the member (x) is impregnated with a solution containing culture medium components; and step (B) of hollowing a part of the layer so that a part of a surface of the container in the concave part is bared to form a hollow.

7. A culturing method using the apparatus of claim 1, comprising:

(1) putting a culture medium solution and cells or a piece of a tissue into the at least one hollow; and (2) culturing the cells or the piece of the tissue.

8. A culturing method using the apparatus of claim 2, comprising:

(1) putting a culture medium solution and cells or a piece of a tissue into the at least one hollow; and (2) culturing the cells or the piece of the tissue.

* * * * *